United States Patent [19]
Ritter et al.

[11] Patent Number: 5,965,537
[45] Date of Patent: Oct. 12, 1999

[54] DOLASTATIN 15 DERIVATIVES WITH CARBONYL AND HETEROCYCLIC FUNCTIONALITIES AT THE C-TERMINUS

[75] Inventors: Kurt Ritter, Newton, Mass.; Wilhelm Amberg, Schwetzingen, Germany; Teresa Barlozzari, Wellesley, Mass.; Andreas Haupt, Northborough, Mass.; Bernd Janssen, Marlborough, Mass.; Andreas Kling, Mannheim, Germany

[73] Assignee: BASF Aktiengesellschaft, Germany

[21] Appl. No.: 08/814,577

[22] Filed: Mar. 10, 1997

[51] Int. Cl.$^6$ ........................................... C07K 5/00
[52] U.S. Cl. ........................... 514/17; 530/330; 530/329; 514/18
[58] Field of Search ...................... 514/17, 18; 530/330, 530/329

[56] References Cited

U.S. PATENT DOCUMENTS

| | | | |
|---|---|---|---|
| 4,816,444 | 3/1989 | Pettit et al. | 514/17 |
| 5,502,032 | 3/1996 | Haupt et al. | 514/17 |
| 5,504,191 | 4/1996 | Pettit et al. | 530/330 |
| 5,530,097 | 6/1996 | Pettit et al. | 530/330 |
| 5,554,725 | 9/1996 | Pettit | 530/330 |

FOREIGN PATENT DOCUMENTS

| | | |
|---|---|---|
| 0 398 558 | 11/1990 | European Pat. Off. . |
| 0 598 129 | 5/1994 | European Pat. Off. . |
| 92/02541 | 2/1992 | WIPO . |
| 93/23424 | 11/1993 | WIPO . |
| 96/40751 | 12/1996 | WIPO . |
| 96/40752 | 12/1996 | WIPO . |
| 97/17364 | 5/1997 | WIPO . |

OTHER PUBLICATIONS

Morrison and Boyd, Organic Chemistry pp. 1004–1006, 1973.

Pettit, G. R., et al., "The Isolation and Structure of a Remarkable Marine Animal Antineoplastic Constituent: Dolastatin 10", *J. Am. Chem. Soc.* 109: 6883–6885 (1987).

Bai, R., et al., "Structure–Activity Studies with Chiral Isomers and with Segments of the Antimitotic Marine Peptide Dolastatin 10", *Biochemical Pharmacology* 40(8): 1859–1864 (1990).

Pettit, G. R., et al., "Antineoplastic Agents. 220. Synthesis of Natural (–)–Dolastatin 15", *J. Am. Chem. Soc.*, 113: 6692–6693 (1991).

Bai, R., et al., "Dolastatin 15, a potent antimitotic depsipeptide derived from *Dolabella auricularia*. Interaction with tubulin and effects on cellular microtubules", *1–Pharmacology* Abstract 117: 103735g p. 41 (1992).

Pettit, G. R., et al., "Isolation and Structure of the Cytostatic Depsipeptide Dolastatin 13 from the Sea Hare *Dolabella auricularia*", *J. Am. Chem. Soc.*, 111(13): 50115–5017 (1989).

Pettit, G. R., et al., "Antineoplastic Agents 337. Synthesis of Dolastatin–10 Structural Modifications," *Anti–Cancer Drug Design*, 10: 529–544 (1995).

Miyazaki, K., et al., "Synthesis and Antitumor Activity of Novel Dolastatin–10 Analogs," *Chem. Pharm. Bull.*, 43(10): 1706–1718 (1995).

Pettit, G. R., et al., "Isolation and Structure of the Cytostatic Linear Depsipeptide Dolastatin 15", *J. Org. Chem.*, 54: 6005–6006 (1989).

Pettit, G.R. et al., "The Dolastatins 20. A convenient Synthetic Route to Dolastatin 15", *Tetrahedron*, 50(42):12097–12108 (1994).

Pettit, G.R. et al., Isolation of Dolastatins 10–15 From the Marine Mollusc *Dolabella Auricularia*, *Tetrahedron*, 49(42):9151–9170 (1993).

*Primary Examiner*—Sheela Huff
*Attorney, Agent, or Firm*—Hamilton, Brook, Smith & Reynolds, P.C.

[57] ABSTRACT

The present invention relates to novel peptides useful as anti-cancer agents. The compounds of the invention are of Formula I, $$A\text{-}B\text{-}D\text{-}E\text{-}F\text{-}G \qquad (I)$$

A, B, D, and E are α-amino acid residues. In one embodiment, F is an azacycloalkanecarboxylic acid residue. In this embodiment, G is a monovalent radical, for example, a hydrogen atom, an alkyl group, an aryl group, or a heteroaryl group. In another embodiment, F is an azacycloalkyl group and G is a heteroaryl group connected to F by a carbon-carbon bond.

In another embodiment, the invention includes a method for treating cancer in a mammal, such as a human, comprising administering to the mammal an effective amount of a compound of Formula I in a pharmaceutically acceptable composition.

21 Claims, No Drawings

DOLASTATIN 15 DERIVATIVES WITH CARBONYL AND HETEROCYCLIC FUNCTIONALITIES AT THE C-TERMINUS

BACKGROUND OF THE INVENTION

A number of short peptides with significant activity as inhibitors of cell growth have been isolated from the Indian Ocean sea hare *Dolabella auricularia* (Bai, et al., *Biochem. Pharmacology*, 40: 1859–1864 (1990); Beckwith, et al., *J. Natl. Cancer Inst.*, 85: 483–488 (1993) and references cited therein). These include Dolastatins 1–10 (U.S. Pat. No. 4,816,444, issued to Pettit, et al.) and Dolastatin-15 (European Patent Application No. 398558). Dolastatin 15, for example, markedly inhibits the growth of the National Cancer Institute's P388 lymphocytic leukemia (PS system) cell line, a strong predictor of efficacy against various types of human malignancies.

The exceedingly small amounts of the various Dolastatin peptides present in *Dolabella auricularia* (about 1 mg each per 100 kg sea hare) and the consequent difficulties in purifying amounts sufficient for evaluation and use, have motivated efforts toward the synthesis of these compounds (Roux, et al., *Tetrahedron*, 50: 5345–5360 (1994); Shioiri, et al., *Tetrahedron*, 49: 1913–24 (1993); Patino, et al., *Tetrahedron*, 48: 4115–4122 (1992) and references cited therein). Synthetic Dolastatin 15, however, suffers from drawbacks which include poor solubility in aqueous systems and the need for expensive starting materials for its synthesis. These, in turn, have led to the synthesis and evaluation of structurally modified Dolastatin 15 derivatives [cf.: *Bioorganic & Med. Chem. Lett.*, 4: 1947–50 (1994); WO 93 03054; JP-A-06234790, WO 93 23 424].

However, there is a need for synthetic compounds with the biological activity of Dolastatin 15 which have useful aqueous solubility and can be produced efficiently and economically.

SUMMARY OF THE INVENTION

Compounds of the present invention include peptides of Formula I,

A-B-D-E-F-G                                            (I), and the acid salts thereof. A, B, D, and E are each an α-amino acid residue, and A is at the amino terminus. In one embodiment, F is an azacycloalkanecarboxylic acid residue. In this embodiment, G is a monovalent radical, for example, a hydrogen atom, an alkyl group, an aryl group, a cycloalkyl, a heteroaryl group, an alkoxyalkyl group, a carboxyl group, a carboxyalkyl group, an aminocarbonylalkyl group, an arylalkyl group, a heteroarylalkyl group, an alkoxycarbonylalkyl group, an aryloxycarbonylalkyl group, an alkylsulfinylalkyl group, an arylsulfinylalkyl group, an alkylsulfonylalkyl group, an arylsulfonylalkyl group, a hydrocarbonyl group, an aryloxycarbonyl group, an alkyl- or arylsulfinyl group or an alkyl- or arylsulfonyl group. In another embodiment, F is an azacycloalkyl group and G is a heteroaryl group connected to F by a carbon-carbon bond.

Another aspect of the present invention includes pharmaceutical compositions comprising a compound of Formula I and a pharmaceutically acceptable carrier.

An additional embodiment of the present invention is a method for treating cancer in a mammal, such as a human, comprising administering to the mammal an effective amount of a compound of Formula I in a pharmaceutically acceptable composition.

DETAILED DESCRIPTION OF THE INVENTION

The present invention relates to peptides having antineoplastic activity. It also includes pharmaceutical compositions comprising these compounds and methods for treating cancer in a mammal, such as a human, by administration of these compositions to the mammal.

Dolastatin 15, a peptide isolated from the sea hare *Dolabella auricularia*, is a potent inhibitor of cell growth. This compound, however, is present only in trace quantities in the sea hare, and is thus difficult to isolate. It is also expensive to synthesize and suffers from poor aqueous solubility. As shown herein, however, Dolastatin 15 can serve as a starting point for the development of compounds which overcome these disadvantages while retaining antineoplastic activity or exhibiting greater antineoplastic activity than the natural product. Applicants have discovered that certain structural modifications of Dolastatin 15 provide compounds with a surprisingly improved therapeutic potential for the treatment of neoplastic diseases as compared to Dolastatins-10 and -15. The Dolastatin-15 derivatives exhibit activity even in multiple drug-resistant tumor systems and an unpredicted high solubility in aqueous solvents. Furthermore, the compounds of the present invention can be conveniently synthesized, as described below in detail.

For the purposes of the present invention, the term "monovalent radical" is intended to mean an electrically neutral molecular fragment capable of forming one covalent bond with a second neutral molecular fragment. Monovalent radicals include the hydrogen atom, alkyl groups, such as methyl, ethyl and propyl groups, halogen atoms, such as fluorine, chlorine and bromine atoms, aryl groups, such as phenyl and naphthyl groups, and alkoxy groups, such as methoxy and ethoxy groups. Two monovalent radicals on adjacent sigma-bonded atoms can also together form a pi bond between the adjacent atoms. Two monovalent radicals may also be linked together, for example, by a polymethylene unit, to form a cyclic structure. For example, the unit —N(R)R', wherein R and R' are each a monovalent radical, can, together with the nitrogen atom, form a heterocyclic ring. In addition, two monovalent radicals bonded to the same atom can also together form a divalent radical, such as an alkylidene group, for example, a propylidene group, or an oxygen atom.

For the purposes of the present invention, the term "residue" refers to the molecular fragment remaining after the removal of the elements of a water molecule (one oxygen atom, two hydrogen atoms) from a molecule, such as an amino acid or a hydroxy acid.

For the purposes of the present invention, the term "normal alkyl" refers to an unbranched, or straight chain, alkyl group, for example, normal propyl (n-propyl, —CH$_2$CH$_2$CH$_3$).

The compounds of the present invention can be represented as Formula I,

A-B-D-E-F-G                                            (I), where A, B, D and E are each an α-amino acid residue. In one embodiment, F is an azacycloalkanecarboxylic acid residue. In this embodiment, G is a monovalent radical selected from the group consisting of hydrogen atom, alkyl groups, alkoxyalkyl groups, carboxyalkyl groups, aminocarbonylalkyl groups, arylalkyl groups, alkoxycarbonylalkyl groups, aminoalkyl groups, aryloxycarbonylalkyl groups, alkylsulfinylalkyl groups, arylsulfinylalkyl groups, alkylsulfonylalkyl groups, arylsulfonylalkyl groups, hydrocarbonyl groups, aryloxycarbonyl groups, alkyl- or arylsulfinyl groups and alkyl- or arylsulfonyl groups. In another embodiment, F is an azacycloalkyl group and G is a heteroaryl group connected to F by a carbon-carbon bond.

The peptides of Formula I are generally composed of L-amino acids, but they can contain one or more D-amino acids. They can also be present as salts with physiologically tolerated acids, including hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and N-acetylglycine.

The following is a description of the present invention, including a detailed description of individual components and of methods of using the claimed compounds.

COMPOUNDS OF THE PRESENT INVENTION

Identity of A

In one embodiment, A is a proline derivative of Formula $II_a$,

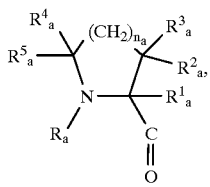

(II$_a$)

where $n_a$ is an integer, preferably 0, 1, 2, or 3. $R_a$ is a monovalent radical, such as a hydrogen atom or a $C_1$–$C_3$-alkyl group which can be normal, branched or cyclic and can be substituted by from 1 to about 3 fluorine atoms; suitable examples include methyl, ethyl, isopropyl, 2-fluoroethyl, 2,2,2-trifluoroethyl, 1-methyl-2-fluoroethyl, 1-fluoromethyl-2-fluoroethyl or cyclopropyl; methyl, ethyl or isopropyl are preferred;

In this embodiment, $R^1_a$ is a monovalent radical, such as a hydrogen atom or a methyl, ethyl, propyl or phenyl group. The phenyl group can be substituted; suitable substituents include one or more halogen atoms, with fluorine, chlorine and bromine being preferred, $C_1$–$C_4$-alkyl groups, methoxy, ethoxy, trifluoromethyl or nitro groups.

$R^2_a$, $R^3_a$, $R^4_a$ and $R^5_a$ are each, independently, a monovalent radical, such as a hydrogen atom or a methyl group. $R_a$ and $R^1_a$ together can also form a propylene bridge.

In another embodiment, A is a substituted glycine derivative of Formula III$_a$,

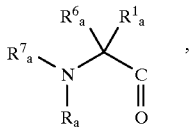

(III$_a$)

where $R_a$ has the meaning stated for Formula II$_a$, $R^1_a$ is a monovalent radical, for example, a hydrogen atom or a lower alkyl group, preferably a methyl, ethyl or propyl group.

In this embodiment, $R^6_a$ is a monovalent radical, such as a hydrogen atom, a normal or branched $C_1$–$C_8$-alkyl group, which can be substituted by up to six halogen atoms, preferably fluorine, or a $C_3$–$C_8$-cycloalkyl or $C_3$–$C_8$-cycloalkyl-$C_1$–$C_4$-alkyl group, a $C_1$–$C_4$-oxoalkyl group such as methoxymethyl, 1-methoxyethyl or 1,1-dimethylhydroxymethyl, a $C_2$–$C_5$ alkenyl group, such as vinyl and 1-methylvinyl, or a substituted or unsubstituted phenyl group. Suitable phenyl substituents include one or more halogen atoms, preferably fluorine, chlorine or bromine, and alkyl, methoxy, ethoxy trifluoromethyl, or nitro groups. $R^7_a$ is a monovalent radical, preferably a methyl group or an ethyl group.

In another embodiment, A is an α-amino acid residue of Formula IV$_a$,

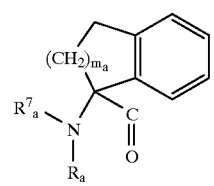

(IV$_a$)

where $m_a$ is an integer, preferably 1 or 2. $R_a$ and $R^7_a$ have the meanings stated for Formula III$_a$.

In another embodiment, A is an α-amino acid residue of Formula V$_a$,

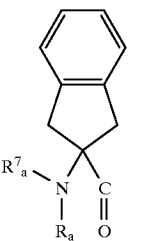

(V$_a$)

where $R_a$ and $R^7_a$ have the meanings stated for Formula III$_a$.

In a further embodiment, A is a substituted proline derivative of Formula VI$_a$,

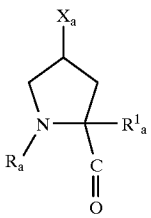

(VI$_a$)

where $R_a$ and $R^1_a$ have the meanings stated for Formula II$_a$, and $X_a$ is a monovalent radical, preferably a hydroxyl, methoxy or ethoxy group or a fluorine atom.

In another embodiment, A is a thiaprolyl derivative of Formula VII$_a$,

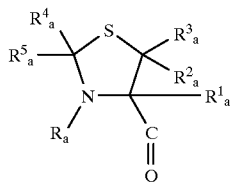

(VII$_a$)

where $R_a$, $R^1_a$, $R^2_a$, $R^3_a$, $R^4_a$ and $R^5_a$ have the meanings stated for Formula II$_a$.

In another embodiment, A is a 1,3-dihydroisoindole derivative of Formula VIII$_a$,

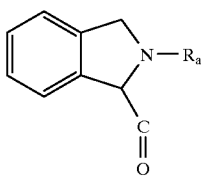

(VIII$_a$)

where $R_a$ has the meaning stated for Formula II$_a$.

In another embodiment, A is a 2-azabicyclo[2.2.1] heptane-3-carboxylic acid derivative of Formula IX$_a$,

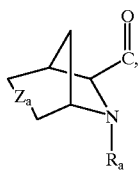

(IX$_a$)

where $Z_a$ is a single or double bond and $R_a$ has the meaning stated for Formula II$_a$. The 3-carbonyl substituent can have either the exo or endo orientation.

Identity of B

B is a valyl, isoleucyl, allo-isoleucyl, norvalyl, 2-tert-butylglycyl or 2-ethylglycyl residue. B can also be a residue of Formula II$_b$,

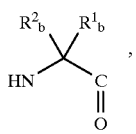

(II$_b$)

in which $R^1_b$ and $R^2_b$ are each a monovalent radical. $R^1_b$ is, preferably, hydrogen and $R^2_b$ is, for example, a cyclopropyl group, a normal or branched butyl, preferably tertiary-butyl, group, a methoxymethyl group, a 1-methoxyethyl group or a 1-methylvinyl group. Additionally, $R^1_b$ and $R^2_b$ together can be an isopropylidene group.

Identity of D

D is an N-alkylvalyl, N-alkyl-2-ethylglycyl, N-alkyl-2-tert-butylglycyl, N-alkyl-norleucyl, N-alkyl-isoleucyl, N-alkyl-allo-isoleucyl or N-alkyl-norvalyl residue, where the alkyl group is preferably methyl or ethyl.

In another embodiment, D is an α-amino carboxylic acid derivative of Formula II$_d$,

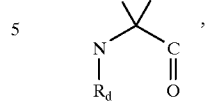

(II$_d$)

where $R_d$ has the meaning stated for $R_a$ in Formula III$_a$, $R^1_d$ is a monovalent radical, preferably a hydrogen atom, and $R^2_d$ is a monovalent radical, such as a cyclopropyl group, a methoxymethyl group, a 1-methoxyethyl group or a 1-methylvinyl group. Additionally, $R^1_d$ and $R^2_d$ together can form an isopropylidene group.

Alternatively, D can be a proline derivative of Formula III$_d$,

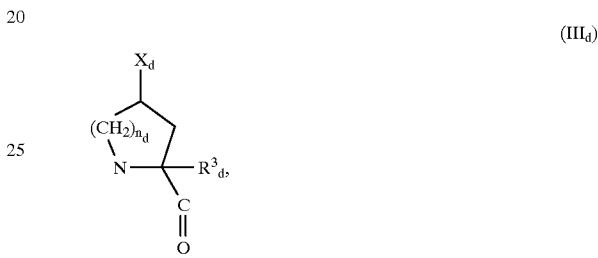

(III$_d$)

where $n_d$ is an integer, for example, 1 or 2, and $R^3_d$ has the meaning stated for $R^1_a$ in Formula III$_a$. $X_d$ is a monovalent radical, preferably a hydrogen atom, and, in the case where $n_d$ equals 1, can also be a hydroxyl, methoxy or ethoxy group or a fluorine atom.

Identity of E

E is a prolyl, thiazolidinyl-4-carbonyl, homoprolyl or hydroxyprolyl residue or a cyclic α-amino carboxylic acid residue of Formula II$_e$,

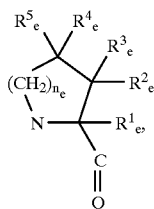

(II$_e$)

where $n_e$ is an integer, preferably 0, 1 or 2. $R^1_e$ has the meaning stated for $R^1_a$ in Formula III$_a$. $R^2_e$ and $R^3_e$ are each a monovalent radical, and can be, independently, a hydrogen atom or a methyl group. $R^4_e$ is a monovalent radical, preferably a hydrogen atom, a hydroxyl, methoxy or ethoxy group or a fluorine atom. $R^5_e$ is a monovalent radical, preferably a hydrogen atom. In the case where $n_e$ has the value 1, $R^3_e$ and $R^4_e$ together can form a double bond or $R^4_e$ and $R^5_e$ can together be a double-bonded oxygen radical. In the case where $n_e$ has the value 1 or 2, $R^1_e$ and $R^2_e$ can together form a double bond.

In another embodiment, E is a 2- or 3-amino-cyclopentanecarboxylic acid residue of Formula III$_e$,

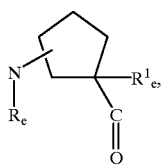

(III_e)

where $R_e$ is a monovalent radical, such as a methyl or ethyl group, and $R^1_e$ has the meaning stated for $R^1_a$ in Formula III$_a$.

Identity of F

In one embodiment of the invention, F is an azacycloalkanecarboxylic acid residue of Formula II$_f$,

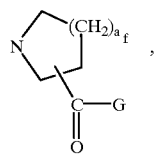

(II_f)

and $a_f$ is an integer, preferably 0, 1, or 2. The carbonyl group is in position 1 or position 2 relative to the nitrogen atom, with position 1 preferred.

In this embodiment, G can be a hydrogen atom, a straight-chain or branched $C_1$–$C_8$-alkyl group, which can be substituted by up to six halogen, preferably fluorine, atoms, or a $C_3$–$C_8$-cycloalkyl or $C_3$–$C_8$-cycloalkyl-$C_1$–$C_4$-alkyl group.

G can also be an arylalkyl, heteroarylalkyl, aryl or heteroaryl group of Formula II$_g$

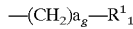 —(CH$_2$)$_{a_g}$—R$^1_1$ (II_g), where $a_g$ is an integer, preferably 0, 1 or 2. $R^1_1$ is a monovalent radical, such as a substituted or unsubstituted aryl, preferably phenyl or naphthyl, group. Suitable aryl group substituents include one or more halogen, preferably fluorine, bromine or chlorine, atoms, $C_1$–$C_4$-alkyl groups, methoxy, ethoxy or trifluoromethyl groups, dioxymethylene, nitro or cyano groups, $C_1$–$C_7$-alkoxycarbonyl, $C_1$–$C_7$-alkylsulfonyl, or amino groups, or $C_1$–$C_6$-dialkylamino groups, where the alkyl groups can together also form a 5- or 6-membered heterocycle. $R^1_1$ can also be an unsubstituted or substituted heteroaryl group, which can be a 5- or 6-membered, preferably nitrogen-, oxygen- or sulfur-containing, ring system, which may be fused to a benzene ring. Examples include heteroaryl groups derived, by removal of a hydrogen atom, from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline residue. Preferred heteroaryl group substituents are one or more $C_1$–$C_6$-alkyl, hydroxyl or phenyl groups.

Another subclass of compounds of this invention includes compounds of Formula I wherein G is an alkoxycarbonylalkyl, aryloxycarbonylalkyl, alkoxycarbonyl or aryloxycarbonyl group of Formula III$_g$,

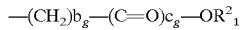 —(CH$_2$)$_{b_g}$—(C=O)$_{c_g}$—OR$^2_1$ (III_g), $b_g$ is an integer, preferably 1, 2 or 3, and $c_g$ is an integer, preferably 0 or 1. $b_g$ and $c_g$ cannot both simultaneously be 0. $R^2_1$ is a monovalent radical, such as a hydrogen atom, a normal or branched $C_1$–$C_8$-alkyl group, which can be substituted by up to six halogen, preferably fluorine, atoms, especially a $CF_2$-moiety, a $C_3$–$C_8$-cycloalkyl group, a $C_3$–$C_8$-cycloalkyl-$C_1$–$C_4$-alkyl group, or a substituted or unsubstituted aryl, preferably phenyl or naphthyl, group. Suitable aryl group substituents include one or more halogen, preferably fluorine, bromine or chlorine, atoms, $C_1$–$C_4$-alkoxy groups, methoxy, ethoxy or trifluoromethyl groups, dioxymethylene, nitro, or cyano groups, $C_1$–$C_7$-alkoxycarbonyl groups, $C_1$–$C_7$-alkylsulfonyl groups, amino groups or $C_1$–$C_6$-dialkylamino groups, where the alkyl groups can, together with the nitrogen atom, also form a 5- or 6-membered heterocycle.

G can also be an aminocarbonylalkyl or aminocarbonyl group of Formula IV$_g$,

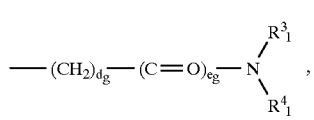

(IV_g)

where $d_g$ is an integer, preferably 1, 2 or 3, and $e_g$ is an integer, preferably 0 or 1. $d_g$ and $e_g$ cannot both simultaneously be 0.

$R^3_1$ and $R^4_1$ are each a monovalent radical which can be selected from, independently from one other, a hydrogen atom, a normal or branched $C_1$–$C_8$-alkyl group, which can be substituted by up to six halogen, preferably fluorine, atoms, especially a $CF_2$-moiety, a $C_3$–$C_8$-cycloalkyl group, a $C_3$–$C_8$-cycloalkyl-$C_1$–$C_4$-alkyl group, or a substituted or unsubstituted aryl, preferably phenyl or naphthyl, group. Suitable aryl substituents include one or more halogen, preferably fluorine, bromine or chlorine, atoms, or one or more $C_1$–$C_4$-alkoxy, trifluoromethyl, dioxymethylene, nitro, cyano, $C_1$–$C_7$-alkoxycarbonyl, $C_1$–$C_7$-alkylsulfonyl, amino or $C_1$–$C_6$-dialkyl-amino groups, where, in the latter, the alkyl groups can, together with the nitrogen atom, also form a 5- or 6-membered heterocycle. $N(R^3_1)R^4_1$ can additionally form a ring system of the formula $N(CH_2)_{f_g}$ where $f_g$ is an integer selected from among 4, 5 or 6.

Another subclass of compounds of this invention includes compounds of Formula I wherein G is an alkyl- or arylsulfinylalkyl, an alkyl- or arylsulfonylalkyl, alkyl- or arylsulfonyl or alkyl- or arylsulfinyl group of Formula V$_g$,

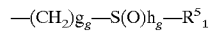 —(CH$_2$)$_{g_g}$—S(O)$_{h_g}$—R$^5_1$ (V_g), where $g_g$ is an integer, for example, 1 or 2. $h_g$ is 1 or 2, while $R^5_1$ is a monovalent radical, preferably a methyl, trifluoromethyl, ethyl or phenyl group.

G can also be an alkyl- or arylcarbonylalkyl group or a hydrocarbonylalkyl group of Formula VI$_g$,

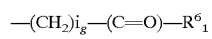 —(CH$_2$)$_{i_g}$—(C=O)—R$^6_1$ (VI_g), where $i_g$ is an integer, for example, 1 or 2; and $R^6_1$ is a monovalent radical, such as a hydrogen atom, a normal or branched $C_1$–$C_8$-alkyl group, which can be unsubstituted or substituted by up to six halogen, preferably fluorine, atoms, a $C_3$–$C_8$-cycloalkyl group; a $C_3$–$C_8$-cycloalkyl-$C_1$–$C_4$-alkyl group; or a substituted or unsubstituted aryl or heteroaryl group, preferably a phenyl group or a naphthyl group. Suitable aryl and heteroaryl substituents include one or more halogen, preferably fluorine, chlorine or bromine, atoms, one or more $C_1$–$C_4$-alkoxy groups, trifluoromethyl, dioxymethylene, nitro or cyano groups, $C_1$–$C_7$-alkoxycarbonyl groups, $C_1$–$C_7$-alkylsulfonyl groups, amino groups or $C_1$–$C_6$-dialkylamino groups, wherein the alkyl groups can, optionally form with the nitrogen atom a 5- or 6-membered heterocycle.

In another embodiment of the present invention, F is an azacycloalkane derivative of Formula $III_f$,

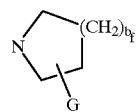

(III$_f$)

wherein $b_f$ is an integer, such as 0, 1 or 2. In this embodiment, G is a heteroaryl group connected to F by a carbon-carbon bond in the 1 or 2, preferably 1, position relative to the nitrogen atom. For example, G can be a heteroaryl group of Formula $VII_g$,

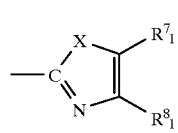

(VII$_g$)

where X is an NH group, an oxygen atom or a sulfur atom. $R^7{}_1$ and $R^8{}_1$ are each a monovalent radical, and can be, independently, a hydrogen atom, a normal or branched $C_1$–$C_8$-alkyl group, which can be substituted by halogen, preferably fluorine, atoms, a $C_3$–$C_8$-cycloalkyl group or a $C_3$–$C_8$-cycloalkyl-$C_1$–$C_4$-alkyl group.

$R^7{}_1$ and $R^8{}_1$ can each also be, independently, a monovalent radical of Formula $II_l$,

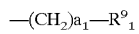

—(CH$_2$)$a_1$—$R^9{}_1$ (II$_l$), where $a_1$ is an integer, preferably 0, 1 or 2, $R^9{}_1$ is a monovalent radical, such as a substituted or unsubstituted aryl group, where aryl is preferably phenyl or naphthyl. Suitable aryl substituents are one or more halogen, preferably fluorine, bromine or chlorine, atoms, $C_1$–$C_4$-alkyl groups, methoxy, ethoxy or trifluoromethyl groups, dioxymethylene, nitro or cyano groups, $C_1$–$C_7$-alkoxycarbonyl, $C_1$–$C_7$-alkylsulfonyl, amino or $C_1$–$C_6$-dialkylamino groups, where in the latter the alkyl groups can, together with the nitrogen atom, form a 5- or 6-membered heterocycle. $R^9{}_1$ can also be an unsubstituted or substituted heteroaryl group, for example, a 5- or 6-membered, preferably nitrogen-, oxygen- or sulfur-containing, ring system, which may be fused to a benzene ring, such as, for example, groups derived, by removal of a hydrogen atom, from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline. Preferred heteroaryl group substituents include one or more $C_1$–$C_6$-alkyl, hydroxyl or phenyl groups.

G can also be a heteroaryl group of Formula $VIII_g$,

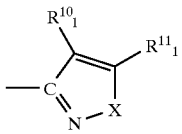

(VIII$_g$)

wherein X is an $NR^{12}{}_1$ group and $R^{12}{}_1$ is a hydrogen atom, a normal or branched $C_1$–$C_8$-alkyl group, which can be substituted by up to six halogen, preferably fluorine, atoms, a $C_3$–$C_8$-cycloalkyl group, or a $C_3$–$C_8$-cycloalkyl-$C_1$–$C_4$-alkyl group; or X is an oxygen atom. $R^{10}{}_1$ and $R^{11}{}_1$ are each, independently, a hydrogen atom, a normal or branched $C_1$–$C_8$-alkyl group, a halogen-substituted normal or branched $C_1$–$C_8$-alkyl group, a $C_3$–$C_8$-cycloalkyl group or a $C_3$–$C_8$-cycloalkyl-$C_1$–$C_4$-alkyl group; or $R^{10}{}_1$ and $R^{11}{}_1$ are, independently, each a monovalent radical of Formula $II_l$, as described above.

G can also be an aromatic diazo group of Formula $IX_g$.

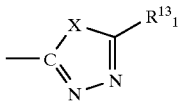

(IX$_g$)

where X is an NH group, an oxygen atom or a sulfur atom, and $R^{13}{}_1$ is a monovalent radical, such as, for example, a hydrogen atom, a normal or branched $C_1$–$C_8$-alkyl group, which can be substituted by up to six halogen, preferably fluorine, atoms, a $C_3$–$C_8$-cycloalkyl group, or a $C_3$–$C_8$-cycloalkyl-$C_1$–$C_4$-alkyl group. $R^{13}{}_1$ can also be a monovalent radical of Formula $II_l$, as described above.

Synthesis of Compounds

The compounds of the present invention can be prepared by known methods of peptide synthesis. Thus, the peptides can be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments in turn can be obtained by sequential assembly from amino acids or by fragment coupling of still shorter peptides.

In both sequential assembly and fragment coupling it is necessary to link the units by forming an amide linkage, which can be accomplished via a variety of enzymatic and chemical methods. Chemical methods for forming the amide linkage are described in detail in standard references on peptide chemistry, including Müller, *Methoden der organischen Chemie* Vol. XV/2, 1–364, Thieme Verlag, Stuttgart, (1974); Stewart and Young, *Solid Phase Peptide Synthesis,* 31–34 and 71–82, Pierce Chemical Company, Rockford, Ill. (1984); Bodanszky, et al., *Peptide Synthesis,* 85–128, John Wiley & Sons, New York, (1976). Preferred methods include the azide method, the symmetric and mixed anhydride method, the use of in situ generated or preformed active esters, the use of urethane protected N-carboxy anhydrides of amino acids and the formation of the amide linkage using coupling reagents, such as carboxylic acid activators, especially dicyclohexylcarbodiimide (DCC), diisopropylcarbodiimide (DIC), 1-ethoxycarbonyl-2-ethoxy-1,2-dihydroquinoline (EEDQ), 1-ethyl-3-(3-dimethylaminopropyl)carbodiimide hydrochloride (EDC), n-propane-phosphonic anhydride (PPA), N,N-bis (2-oxo-3-oxazolidinyl)imido-phosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N', N'-tetramethyluronium salts (HBTU), diethylphosphoryl cyanide (DEPCN), 2,5-diphenyl-2,3-dihydro-3-oxo-4-hydroxy-thiophene dioxide (Steglich's reagent; HOTDO), and 1,1'-carbonyl-diimidazole (CDI). The coupling reagents can be employed alone or in combination with additives such as N. N-dimethyl-4-aminopyridine (DMAP), N-hydroxy-benzotriazole (HOBt), N-hydroxybenzotriazine (HOOBt), N-hydroxysuccinimide (HOSu) N-hydroxyazabenzotriazole (HOAt), azabenzotriazolyl-tetramethyluronium salts (HATU, HAPyU) or 2-hydroxypyridine.

Although the use of protecting groups is generally not necessary in enzymatic peptide synthesis, reversible protection of reactive groups not involved in formation of the amide linkage is necessary for both reactants in chemical synthesis. Three conventional protective group techniques are preferred for chemical peptide synthesis: the benzyloxycarbonyl (Z), the t-butoxycarbonyl (Boc) and the 9-fluorenylmethoxycarbonyl (Fmoc) techniques. Identified in each case is the protective group on the α-amino group of the chain-extending unit. A detailed review of amino-acid protective groups is given by Müller, Methoden der organischen Chemie Vol. XV/1, pp. 20–906, Thieme Verlag, Stuttgart (1974). The units employed for assembling the peptide chain can be reacted in solution, in suspension or by a method similar to that described by Merrifield in *J. Am. Chem. Soc.*, 85: 2149 (1963). Particularly preferred methods are those in which peptides are assembled sequentially or by fragment coupling using the Z, Boc or Fmoc protective group technique, with one of the reactants in the said Merrifield technique being bonded to an insoluble polymeric support (also called resin hereinafter). This typically entails assembling the peptide sequentially on the polymeric support using the Boc or Fmoc protective group technique, with the growing peptide chain covalently bonded at the C terminus to the insoluble resin particles. This procedure allows the removal of reagents and byproducts by filtration, eliminating the need to recrystallize intermediates.

The protected amino acids can be linked to any suitable polymer, which must be insoluble in the solvents used and to have a stable physical form which permits filtration. The polymer must contain a functional group to which the first protected amino acid can be covalently attached. A wide variety of polymers are suitable for this purpose, including cellulose, polyvinyl alcohol, polymethacrylate, sulfonated polystyrene, chloromethylated styrene/divinylbenzene copolymer (Merrifield resin), 4-methylbenzhydrylamine resin (MBHA-resin), phenylacetamidomethyl resin (Pam-resin), p-benzyloxy-benzyl-alcohol-resin, benzhydryl-amine-resin (BHA-resin), 4-(hydroxymethyl-)-benzoyl-oxymethyl-resin, the resin of Breipohl, et al. (*Tetrahedron Letters*, 28: 565 (1987); supplied by BACHEM), 4-(2,4-dimethoxyphenylaminomethyl) phenoxy resin (supplied by Novabiochem) or o-chlorotrityl-resin (supplied by Biohellas).

Solvents suitable for peptide synthesis include any solvent which is inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of these solvents.

Peptide synthesis on the polymeric support can be carried out in a suitable inert organic solvent in which the amino acid derivatives starting materials are soluble. However, preferred solvents additionally have resin-swelling properties, such as DMF, DCM, NMP, acetonitrile and DMSO, and mixtures of these solvents. Following synthesis, the peptide is removed from the polymeric support. The conditions under which this cleavage is accomplished for various resin types are disclosed in the literature. The cleavage reactions most commonly used are acid- or palladium-catalyzed, the former being conducted in, for example, liquid anhydrous hydrogen fluoride, anhydrous trifluoromethanesulfonic acid, dilute or concentrated trifluoroacetic acid, and acetic acid/dichloromethane/trifluoroethanol mixtures. The latter can be carried out in THF or THF-DCM-mixtures in the presence of a weak base such as morpholine. Certain protecting groups are also cleaved off under these conditions.

Partial deprotection of the peptide may also be necessary prior to certain derivatization reactions. For example, peptides dialkylated at the N-terminus can be prepared either by coupling the appropriate N,N-dialkylamino acid to the peptide in solution, by reductive alkylation of the resin-bound peptide in DMF/1% acetic acid with NaCNBH$_3$ and the appropriate aldehyde or by hydrogenation with Pd/C in presence of an aldehyde or ketone.

The three schemes which follow present a more detailed description of the synthesis of the compounds of the present invention.

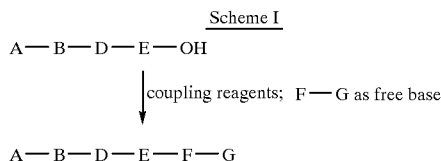

Here, the tetrapeptide A-B-D-E-OH is coupled with an azacycloalkyl derivative, F-G, using the methods for peptide coupling discussed above.

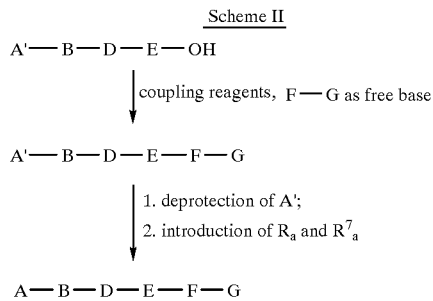

Here, the N-terminal protected tetrapeptide A'-B-D-E-OH is coupled with an azacycloalkyl derivative F-G to give an intermediate compound A'-B-D-E-F-G using the methods for peptide coupling described above. The N-protecting group is then removed by conventional methods as described above. The groups $R_a$ and $R^7_a$ can then be attached to the amino terminus via reductive alkylation as described above.

Scheme III

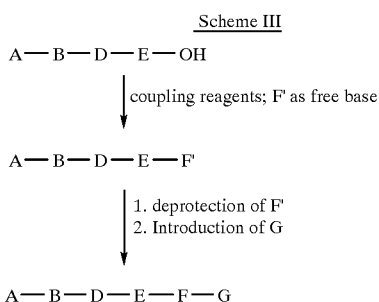

In Scheme 3 the tetrapeptide is coupled with F', a protected form of the building block F. F can also be attached to a precursor of the group G. The intermediate A-B-D-E-F' is then transformed into the final product by a reaction such as an oxidation reaction or a reduction reaction. In one embodiment, F' is a pyrrolidinyl alcohol, and the intermediate A-B-D-E-F' is oxidized to the final product by a mild oxidation process, such as the Swern oxidation, or oxidation with the Dess-Martin reagent.

Building blocks of use in the synthesis of the claimed compounds can be prepared by the following general methods:

(a) Pyrrolidinyl-ketones and piperidinyl-ketones

Several routes to pyrrolidinyl-ketones have been described in literature. Racemic pyrrolidinyl-ketones can be obtained by hydrogenation of the corresponding pyrrolyl ketones with platinum oxide as catalyst (Kaiser, et al., *J. Org. Chem.*, 49: 4203 (1984)). For chiral pyrroldinyl-ketones L- or D-proline could be used as starting material. As protecting group for the ring nitrogen tert. butyloxycarbonyl group (boc-group), the benzyloxy carbonyl (Z-group) or the fluorenyloxy-carbonyl group (fmoc group) could be used.

The N-Boc-protected pyrrolidinyl-ketones can be obtained by treatment of proline derivatives, especially the N-Boc-proline-2-thiopyridyl ester or N-Boc-proline N-methoxy-N-methylamide, with organometallic reagents, such as Grignard reagents or lithium reagents. Several examples have been reported in literature, including N-Boc-pyrrolidinyl methyl ketone from N-Boc-proline N-methoxy-N-methylamide (Trost, *J. Am. Chem. Soc.*, 111: 4988 (1989)); N-Boc-pyrrolidinyl-pentafluoroethyl-ketone from N-Boc-proline N-methoxy-N-methylamide (Angelastro, M. R., et al., *Tetrahedron Letters*, 33: 3265 (1992)); and N-Boc-pyrrolidinyl methyl ketone from N-Boc-proline 2-thiopyridyl ester (Conrow, R., et al., *J. Org. Chem.*, 51: 938 (1986)).

Removal of the Boc-protecting group could be achieved by treatment with strong acids as HCl (see, for example Angelastro, M. R., et al., *Tetrahedron Letters*, 33: 3265 (1992)), or trifluoroacetic acid (see for example, Goldstein, S. W., et al., *J. Org. Chem.*, 57: 1179 (1992)). The alkyl and aryl-pyrrolidinyl-ketones have been prepared by this method.

A second approach to these building blocks involves treating the Boc-protected proline aldehyde with a nucleophilic reagent to produce the corresponding alcohol. This alcohol could be deprotected and coupled to a peptide in the usual fashion. Oxidation of the alcohol could be achieved by mild oxidation procedures such as the Swern oxidation or oxidation with the Dess-Martin reagent. An example of a synthesis of a peptide containing a pyrrolidino-thiazolyl ketone is disclosed in Tsutsumi, S., et al., *Bioorg. Med. Chem. Lett.*, 4: 831 (1994). Alternatively the alcohol could be oxidized first to the ketone followed by removal of the N-protecting group. The trifluoromethylation of aldehydes with commercially available trifluoromethyl-trimethylsilane is catalyzed by tetrabutylammonium fluoride (Olah, G., *J. Am. Chem. Soc.*, 111: 393 (1989)). After deprotection and coupling to tetrapeptide the alcohol can be oxidized to the ketone by mild oxidation procedures such as the Swern oxidation or oxidation with the Dess-Martin reagent.

Different $\alpha$-, $\beta$- and $\gamma$-dicarbonyl derivatives of proline have been described. Thus, (S)-1-pyrrolidinyl)-1,2-propanedione hydrochloride has been obtained from the Boc-protected derivative by treatment with HCl (Conrow, R., et al., *J. Org. Chem.*, 51: 938 (1986)). The ethyl N-Boc-pyrrolidinyl-$\beta$-ketoacetate was obtained by addition of lithio ethylacetate to the N-Boc protected prolinal and subsequent oxidation, for example with chromium trioxide. (Hanson, G. J., et al., *Tetrahedron Letters*, 27: 3577 (1986)). The preparation of $\beta$-ketodifluoroesters from amino acid derivatives has been described (*J. Med. Chem.*, 35: 4795 (1992)), and is similiar to the procedures described above for the ketoester, using the Reformatsky reagent of bromodifluoroacetate in the first step and the Dess-Martin-reagent for the oxidation step.

Methods similar to those described above for pyrrolidinyl-ketones can be used for the synthesis of piperidinyl-ketones and ketones with a seven membered azaheterocycle. Starting materials for these syntheses include pipecolinic acid, all three isomers of which are commercially available, and for 2-pipecolinic acid the enantiomers as well. For example, the methyl ketone has been prepared by treatment of the N-Boc-((2-pyridylthio) carbonyl)-piperidine with the methyl Grignard reagent (*J. Am. Chem. Soc.*, 115: 11393 (1993)).

(b) Pyrrolidinyl-oxazoles and piperidinyl-oxazoles

Several synthetic approaches to oxazoles derived from amino acids have been described in the literature. In general, the N-protected aminoacids are coupled with aminoketones or other 2-amino-carbonyl derivatives using conventional methods for peptide synthesis as described above. For example, the Z- or the Boc-protecting group can be used to protect amino nitrogen. Then, water is removed from the $\beta$-ketoamides of the amino acids to yield the corresponding oxazoles. Several reagents have been used for the dehydration of these compounds, including phosphorus pentoxide, phophorus trichloride, phosphorus pentachloride and thionyl chloride. Another preferred method is the use of a phosphine such as trialkyl- or triarylphosphine, preferably triphenylphoshine, in combination with a halogenated hydrocarbon, preferably chloro- or bromohydrocarbon such as tetrachloromethane, tetrabromomethane, chloroform and perchloroethane in presence of a base such as triethylamine, diazabicycloundecene, methyl-morpholine or pyridine in polar solvents such as acetonitrile. For example, a tryptophan-derived oxazole has been pepared according to this method (Gordon, T. D., et al., *Tetrahedron Letters*, 34: 1901 (1993)). Also the combination of triphenylphosphine, iodine and triethylamine have been reported to give good yields of oxazoles (Wipf, P., et al. ,*J. Org. Chem.*, 58: 3604 (1993)).

Another method of forming the oxazoles involves coupling the aminoacids with 2-aminoalcohols using the usual methods of amide bond formation in peptide synthesis. The cyclization to oxazolines can be achieved by using Burgess reagent, (methyl N-(triethylammonio-sulfonyl)carbamate) (Wipf, P., et al. , *Tetrahedron Letters*, 33: 907 (1992); Wipf, P., et al., *J. Am. Chem., Soc.,* 114: 01975 (1992); Wipf, P., et al., *J. Org. Chem.,* 58: 1575 (1993)) or the Mitsunobu reaction (triphenylphosphine/diisopropyl azodicarboxylate) (Wipf, P., et al., *Tetrahedron Letters,* 33: 6267 (1992)). Oxidation to the oxazole can be carried out using nickelperoxide (Evans, D. L., et al., *J. Org. Chem.,* 44: 497 (1979)).

These methods could also be used for the synthesis of the corresponding pyrrolidinyl-oxazole starting with either N-protected D- or L-proline, and the corresponding piperidinyl-oxazoles, starting with N-protected D- or L-pipecolinic acid.

Following oxazole formation the N-protecting group can be removed, for example, by treating Boc-protected compounds with acids such as hydrochloride or trifluoroacetic acid. The resulting salt or the free base can then be used in the next coupling step.

(c) Pyrrolidinyl-thiazole and piperidinyl-thiazoles

A general method for the synthesis of thiazoles is the Hantzsch synthesis, which involves condensation of N-protected thioamides of amino acids with substituted halo-pyruvates. This reaction, however, is usually accompanied by racemization at the amino acid moiety. Milder methods have been developed to avoid racemisation. First, the N-protected aminoacids are coupled with aminoketones or other 2-amino-carbonyl derivatives using the conventional methods for peptide synthesis as described above. Thionation, cyclization and dehydration can be achieved in a single pot reaction using Lawesson's reagent (Gordon, T. D., et al., *Tetrahedron Letters,* 34: 1901 (1993)) at high temperatures, for example in refluxing tetrahydrofuran.

Thiazolines can be synthesized as follows: first, the corresponding N-protected amino acid is coupled with a 2-siloxyethylamine using the usual methods of amide bond formation in peptide synthesis. After thionation of the amide by Lawesson's reagent, the silyl group is removed and cyclization to the thiazoline is achieved by using either Burgess reagent (methyl N-(triethylammonio-sulfonyl) carbamate) or the Mitsunobu reaction (triphenyl-phosphine/diisopropyl azodicarboxylate) (Wipf, P., et al., *Tetrahedron Letters,* 33: 6267 (1992)).

(d) pyrrolidinyl-imidazoles and piperidinyl-imidazoles

Imidazoles can be prepared from the β-ketoamides of the corresponding amino acids by treatment with an ammonium salt or an amine followed by dehydration using a dehydrating agent or azeotropic removal of water (Gordon, T. D., et al., *Tetrahedron Letters,* 34: 1901 (1993)).

(e) pyrrolidinyl-isoxazoles and piperidinyl-isoxazoles

Isoxazoles can be prepared by reaction of hydroxylamine with 1,3-diketones, the cyclization of 3-keto-oximes or by 1,3-dipolar cycloaddition of N-oxides to alkynes. The synthesis of 5-(N-methyl-pyrroldinyl)-3-methyl-isoxazol has been described by cyclization of (N-methyl-pyrrolidin-2-yl)-4-oxo-butyl-2-oxime using methanesulfonyl-chloride and triethylamine as base (Elliott, R., et al. *Synthesis,* 7: 772 (1950)).

Methods for the preparation of nitrile oxides and the corresponding isoxazoles are described in K. B. G. Torssell, *Nitrile Oxides, Nitrones and Nitronates in Organic Synthesis,* VCH Verlagsgesellschafft, Weinheim.

(f) pyrrolidinyl-pyrazoles and piperidinyl-pyrazoles

Pyrazoles can be prepared by the reaction of hydrazine or monosubstituted hydrazines with the corresponding 1,3-diketones or 3-ketoacetonitrile in a polar solvent such as an alcohol or N,N-dimethylformamide. Synthesis of pyrrolidinyl-ketones has been described. For example, 2-methyl-5-(1-methylpyrrolidin-2-yl)-2H-pyrazol-3-yl-amine was prepared from the corresponding nitrile and hydrazine. (Adachi, et al., *Chem. Pharm. Bull.,* 35: 3235 (1987)).

(g) pyrrolidinyl-oxadiazoles and piperidinyl-oxadiazoles

Pyrrolidinyl-oxadiazoles and piperidinyl-oxadiazoles can be prepared by dehydration of the corresponding diacylhydrazines with phosphoric anhydride and traces of an acid, such as methanesulfonic acid or with hexamethyldisilazane and tetrabutylammonium fluoride. (Rigo, et al., *J. Heterocycl. Chem.,* 23: 253 (1986); Rigo, et al., *Synth. Comm.,* 16: 1665 (1986)). The diacylhydrazines are prepared by coupling of the corresponding N-protected carboxylic acids and the hydrazide of another carboxylic acid. (Sheradsky, et al., *Tet. Lett.,* 32: 133 (1991)). Another mild method is reaction of the hydrazine with thionyl chloride and pyridine to form the 1,2,3,4-oxathiadiazole-S-oxide intermediate. The 1,3,4-oxadiazole is then formed by thermal elimination of sulfur dioxide (Borg, et al., *J. Org. Chem.,* 60: 3112 (1995)).

(h) pyrrolidinyl-thiodiazoles and piperidinyl-thiodiazoles

Pyrrolidinyl-1,3,4-thiadiazoles and piperidinyl-1,3,4-thiadiazoles can be obtained by reaction of the corresponding hydrazones with Lawesson's reagent or $P_4S_{10}$ (Sawtney, et al., *J. Indian Chem. Soc.* B, 30: 407 (1991); Lancelot, et al., *J. Heterocycl. Chem.,* 17: 625 (1980)). The acylhydrazines are prepared as described above.

Methods of Use of the Claimed Compounds

In another embodiment, the present invention comprises a method for partially or totally inhibiting formation of, or otherwise treating (e.g., reversing or inhibiting the further development of) solid tumors (e.g., tumors of the lung, breast, colon, prostate, bladder, rectum, or endometrial tumors) or hematological malignancies (e.g., leukemias, lymphomas) in a mammal, for example, a human, by administering to the mammal a therapeutically effective amount of a compound or a combination of compounds of Formula I. The agent may be administered alone or in a pharmaceutical composition comprising the agent and an acceptable carrier or diluent. Administration may be by any of the means which are conventional for pharmaceutical, preferably oncological, agents, including oral and parenteral means such as subcutaneously, intravenously, intramuscularly and intraperitoneally, nasally or rectally.

The dosage to be administered to the mammal, such as a human, will contain a therapeutically effective amount of a compound described herein. As used herein, "therapeutically effective amount" is an amount sufficient to inhibit (partially or totally) formation of a tumor or a hematological malignancy or to reverse development of a solid tumor or other malignancy or prevent or reduce its further progression. For a particular condition or method of treatment, the dosage is determined empirically, using known methods, and will depend upon factors such as the biological activity of the particular compound employed; the means of administration; the age, health and body weight of the recipient; the nature and extent of the symptoms; the frequency of treatment; the administration of other therapies; and the effect desired. A typical daily dose will be from about 1 to about 50 milligrams per kilogram of body weight by oral administration and from about 0.5 to about 20 milligrams per kilogram of body weight by parenteral administration.

The compounds of the present invention can be administered in conventional solid or liquid pharmaceutical administration forms, eg. uncoated or (film-)coated tablets, capsules, powders, granules, suppositories or solutions. These are produced using known methods. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained re-lease compositions, antioxidants and/ or propellant gases (cf. H. Sucker et al.: *Pharmazeutische Technologie,* Thieme-Verlag, Stuttgart, 1978). The administration forms obtained in this way typically contain from about 1 to about 90% by weight of the active substance.

The following examples are intended to illustrate the invention but are not to be considered limitations of the invention.

EXAMPLES

The proteinogenous amino acids are abbreviated in the examples using the known three-letter code. Other abbreviations employed are: TFA=trifluoroacetic acid, Ac=acetic acid, DCM=dichloromethane, DMSO=dimethylsulfoxide, Bu=butyl, Et=ethyl, Me=methyl, Bzl=benzyl. In the compounds listed, all proteinogenous amino acids are L-amino acids unless otherwise noted.

General materials and methods

The tetrapeptides of the formula A-B-D-E-OH or A'-B-D-E-OH of the present invention, wherein A' means a N-protected from of A, or the corresponding esters are synthesized by classical solution synthesis using standard Z- or Boc-methodology as discussed above. A general route to these tetrapeptides has been described in German Patent Application No. DE 4415998, especially the tetrapeptides Z-Val-Val-MeVal-Pro-OMe; $Me_2$Val-Val-MeVal-Pro-OMe x HCl; Z-Ile-Ile-MeVal-Pro-OMe and $Me_2$Ile-Ile-MeVal-Pro-OMe.

The acids of these tetrapeptides could be obtained by basic hydrolysis of the ester with sodium or lithium hydroxide as described in DE 4415998.

Furthermore, the tetrapeptides of the present invention are synthesized by standard methods of solid-phase synthesis on a completely automatic model 431A synthesizer supplied by APPLIED BIOSYSTEMS. The apparatus uses different synthetic cycles for the Boc and Fmoc protective group techniques, as described below.

Synthetic cycle for the Boc protecting group technique

| 1. | 30% trifluoroacetic acid in DCM | 1 × 3 min |
|---|---|---|
| 2. | 50% trifluoroacetic acid in DCM | 1 × 1 min |
| 3. | DCM washing | 5 × 1 min |
| 4. | 5% diisopropylethylamine in DCM | 1 × 1 min |
| 5. | 5% diisopropylethylamine in NMP | 1 × 1 min |
| 6. | NMP washing | 5 × 1 min |
| 7. | Addition of preactivated protected amino acid (activation with 1 equivalent of DCC and 1 equivalent of HOBt in NMP/DCM); Peptide coupling (1st part) | 1 × 30 min |
| 8. | Addition of DMSO to the reaction mixture until it contains 20% DMSO by volume | |
| 9. | Peptide coupling (2nd part) | 1 × 16 min |
| 10. | Addition of 3.8 equivalents of diisopropylethylamine to the reaction mixture | |
| 11. | Peptide coupling (3rd part) | 1 × 7 min |
| 12. | DCM washing | 3 × 1 min |
| 13. | if conversion is incomplete, repetition of coupling (back to step 5) | |
| 14. | 10% acetic anhydride, 5% diisopropylethylamine in DCM | 1 × 2 min |
| 15. | 10% acetic anhydride in DCM | 1 × 4 min |
| 16. | DCM washing | 4 × 1 min |
| 17. | back to step 1. | |

BOP-Cl and PyBrop were used as reagents for coupling an amino acid to an N-methylamino acid. The reaction times were correspondingly increased. In solution synthesis, the use of either Boc-protected amino acid NCAs (N-tert-butyloxycarbonyl-amino acid-N-carboxy-anhydrides) or Z-protected amino acid NCAs (N-benzyloxycarbonyl-amino acid-N-carboxy-anhydrides), respectively, is most preferable for this type of coupling.

Synthetic cycle for the Fmoc protective group technique

| 1. | DMF washing | 1 × 1 min |
|---|---|---|
| 2. | 20% piperidine in DMF | 1 × 4 min |
| 3. | 20% piperidine in DMF | 1 × 16 min |
| 4. | DMF washing | 5 × 1 min |
| 5. | Addition of the preactivated protected amino acid (activation by 1 equivalent of TBTU and 1.5 equivalent of DIPEA in DMF); Peptide coupling | 1 × 61 min |
| 6. | DMF washing | 3 × 1 min |
| 7. | if conversion is incomplete, repetition of coupling (back to 5.) | |
| 8. | 10% acetic anhydride in DMF | 1 × 8 min |
| 9. | DMF washing | 3 × 1 min |
| 10. | back to 2. | |

BOP-Cl and PyBrop were used as reagents for coupling an amino acid to an N-methylamino acid. The reaction times were correspondingly increased.

Reductive alkylation of the N terminus

The peptide-resin prepared as described above was deprotected at the N terminus and then reacted with a 3-fold molar excess of aldehyde or ketone in DMF/1 acetic acid with addition of 3 equivalents of $NaCNBH_3$. After reaction was complete (negative Kaiser test), the resin was washed several times with water, isopropanol, DMF and dichloromethane.

Workup of the peptide-resins

The peptide-resin obtained via the Boc protecting group method was dried under reduced pressure and transferred into a reaction vessel of a TEFLON HF apparatus (supplied by PENINSULA). A scavenger, usually anisole (1 ml/g of resin), was then added and additionally, in the case of tryptophan-containing peptides, a thiol (0.5 ml/g of resin), preferably ethanedithiol, to remove the indolic formyl group. This was followed by condensing in hydrogen fluoride (10 ml/g of resin) in a bath of liquid $N_2$. The mixture was allowed to warm to 0° C. and stirred at this temperature for 45 min. The hydrogen fluoride was then stripped off under reduced pressure, and the residue was washed with ethyl acetate to remove any remaining scavenger. The peptide was extracted with 30% acetic acid and filtered, and the filtrate was lyophilized.

The peptide-resin obtained via the Fmoc protecting group method was dried under reduced pressure and then subjected to one of the following cleavage procedures, depending upon the amino-acid composition (Wade, Tregear, Howard Florey Fmoc Workshop Manual, Melbourne 1985). The suspension of the peptide-resin in the suitable TFA mixture was stirred at room temperature for the stated time and then the resin was filtered off and washed with TFA and DCM. The filtrate and the washings were concentrated, and the peptide was precipitated by addition of diethyl ether. :After cooling in an ice bath, the precipitate was filtered off, taken up in 30% acetic acid and lyophilized.

When an o-chlorotrityl-resin (supplied by Biohellas) was used, the suspension of the peptide-resin in an acetic acid/trifluoroethanol/dichloromethane mixture (1:1:3) was stirred at room temperature for 1 hr. The suspension was then filtered with suction and the peptide-resin was thoroughly washed with the cleavage solution. The combined filtrates were concentrated in vacuo and treated with water. The precipitated solid was removed by filtration or centrifugation, washed with diethyl ether and dried under reduced pressure.

Purification and characterization of the peptides

Purification was carried out by gel chromatography (SEPHADEX G-10, G-15/10% HOAc, SEPHADEX LH20/ MeOH) with or without subsequent medium pressure chromatography (stationary phase: HD-SIL C-18, 20–45 m, 100 Å; mobile phase: gradient with A=0.1% TFA/MeOH, B=0.1% TFA/H2O). The purity of the resulting products was determined by analytical HPLC (stationary phase: 100 2.1 mm VYDAC C-18, 5 1, 300 Å; mobile phase: CH3CN/H2O gradient, buffered with 0.1% TFA, 40%C).

The polypeptides were characterized by fast atom bombardment mass spectroscopy.

Example 1

Synthesis of a Pyrrolidinyl Ketone (a) Synthesis of N-Methyl-N-methoxy-(Boc-proline)-amide

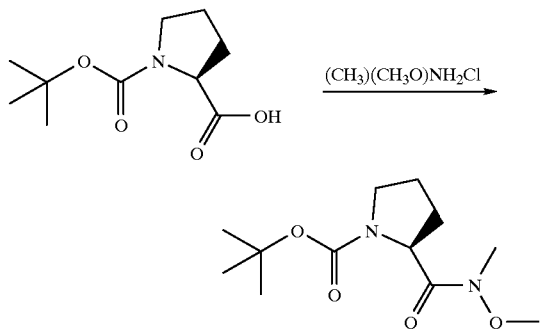

To a solution of 30 g Boc-proline and 13.6 g N,O-dimethylhydroxylamine hydrochloride in 250 ml of dichloromethane was added 26.73 g 1-ethyl-3-(3-dimethylaminopropyl) carbodiimide hydrochloride, 18.83 g N-hydroxy-benzotriazol and 49.34 g N-methyl-morpholine at 0° C. The mixture was stirred overnight at room temperature. The reaction mixture was washed sequentially with saturated sodium bicarbonate, a 5% aqueous solution of citric acid and brine. The organic phase was dried over sodium sulfate. After filtration, the solvent was removed in vacuo to give 22.9 g N-methyl-N-methoxy-(Boc-proline)-amide.

$^1$H-NMR (CDCl$_3$, 270 MHZ) d=1.4, 1.45 (s, 9 H), 1.8–2.3 (m, 4 H), 3.2 (s, 3 H), 3.3–3.6 (m, 2H), 3.7 (s, 3 H), 3.8 (s, 3 H), 4.6, 4.7 (d, 1 H) ppm (b) Preparation of (S)-Boc-pyrrolidin-2-yl-methylketone

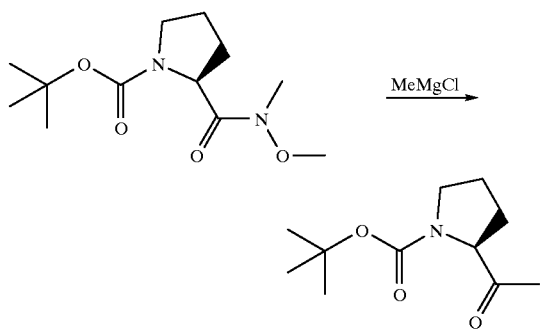

To a solution of 2.0 g N-methyl-N-methoxy-(Boc-proline)-amide in 70 ml tetrahydrofuran a 3 ml portion of 3M methylmagnesium chloride in tetrahydrofuran was added dropwise at −40° C. The mixture was then allowed to warm to room temperature and stirred overnight. The solution was diluted with diethyl ether, washed with brine and dried over sodium sulfate. After filtration, the solvent was removed in vacuo. The residue was purified by silica gel chromatography (heptane/ethyl acetate 2:1) to yield 1.66 g (S)-Boc-pyrrolidin-2-yl-methylketone $^1$H-NMR (CDCl$_3$, 270 MHZ) d=1.4, 1.45 (s, 9 H), 1.75–1.9 (m, 4 H), 2.1, 2.15 (s, 3 H), 3.4–3.6 (m, 2H), 4.2, 4.3 (d, 1 H) ppm (c) Preparation of (S)-pyrrolidin-2-yl-methylketone trifluoroacetic acid salt

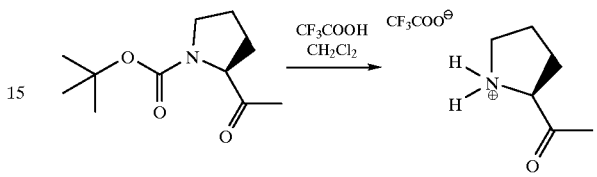

To a solution of 1.66 g (S)-Boc-pyrrolidin-2-yl-methylketone in 25 ml of dichloromethane was added a 25 ml portion of trifluoroacetic acid. The resulting mixture was stirred at room temperature for three-hours. Removal of the solvent provided 0.80 g crude (S)-pyrrolidin-2-yl-methylketone trifluoroacetic acid salt.

$^1$H-NMR (DMSO, 270 MHZ) d=1.75–2.0 (m, 4 H), 2.2 (s, 3 H), 3.1 (m, 2 H), 4.5 (d, 1 H), 8.7 (m, 1H), 10.4 (m, 1 H) ppm

Example 2

Preparation of a Pyrrolidinyl Heterocycle (a) Synthesis of N-(N'-BOC-pyrrolidinyl)methylphenylketone

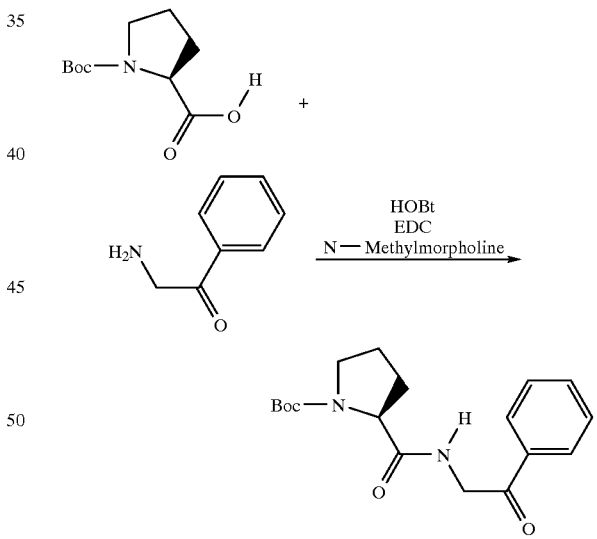

BOC-pro-OH (6.2 g, 29 mmol) and 2-amino-acetophenone.HCl (5.0 g, 29 mmol) were dissolved in 290 mL dry CH$_2$Cl$_2$ and the resulting solution was cooled to 0° C. HOBT.H$_2$O (1.4 g, 9.6 mmol) EDC.HCL were added, followed by NMM (3.8 mL, 35 mmol). The reaction mixture was stirred overnight at room temperature, then washed with saturated sodium bicarbonate (3x), water (3x), 5% citric acid, and water. After drying over sodium sulfate, the solvent was removed under reduced pressure, affording 9.5 g of a yellow oil. Upon dissolution of the oil in diisopropyl ether, the product precipitated as white crystals, which were dried and used directly in the next step. Yield: 8.6 g (89%).

¹H NMR (DMSO-d₆) : 8.1–8.25, m, 1H; 8.0, d, 2H; 7.65, t, 1H; 7.5, t, 2H; 4.5–4.7 ,m, 2H; 4.1–4.25, m, 1H; 3.2–3.5, m, 2H; 2.0–2.2, m, 1H; 1.7–1.9, m, 3H; 1.3 and 1.4, s, together 9H.

(b) Preparation of 2-(N-BOC-pyrrolidinyl)-4-phenyloxazole

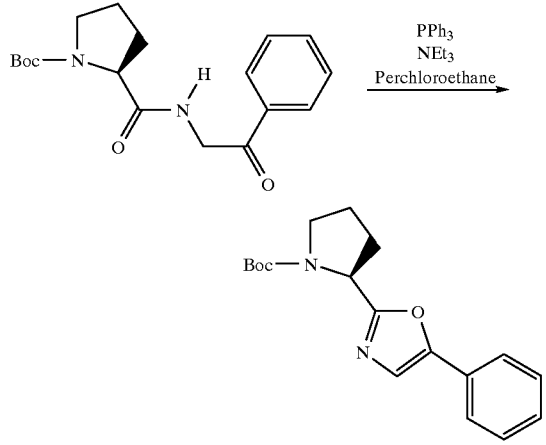

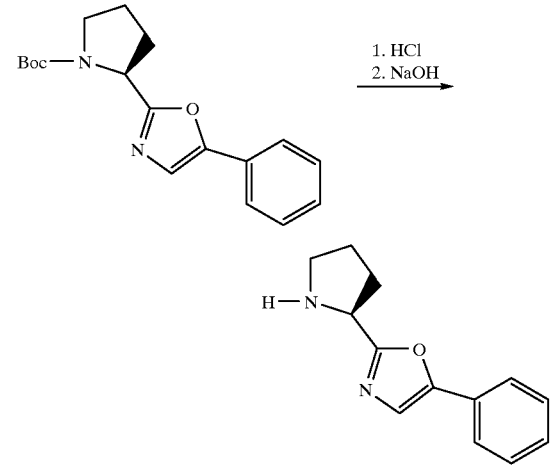

N-(N'-BOC-pyrrolidinyl)methylphenylketone (2.5 g, 7.5 mmol) was dissolved under dinitrogen in 40 mL dry acetonitrile. The mixture was cooled to −20° C., then triphenylphosphine (4.0 g, 15 mmol) perchloroethane (3.6 g, 15 mmol) and triethylamine (4.3 mL, 30 mmol) were added. After stirring overnight at room temperature, the reaction mixture was diluted with ethyl acetate and washed with saturated aqueous sodium carbonate, 5% citric acid and brine. After drying over sodium sulfate, the solvent was removed under reduced pressure, and the resulting crude solid was purified by chromatography on silica gel, affording 1.5 g (64%) of a light brown solid.

¹H NMR (DMSO-d₆): 7.6–7.8, m, 3H; 7.5, t, 2H; 7.4, t, 1H; 4.8–5.0, m, 1H; 3.45–3.6, m, 1H; 3.3–3.45, m, 1H; 2.2–2.4, m, 1H; 1.8–2.1, m, 3H; 1.2 and 1.4, s, together 9H.

(c) Deprotection of 2-(N-BOC-pyrrolidinyl)-4-phenyloxazole

The BOC protected compound 3 (100 mg, 0.3 mmol) was dissolved in 10 mL dry diethylether and treated with 12 mL HCl-saturated ether. The resulting suspension was stirred at room temperature for five days. The pH was then adjusted to 11 with 2N NaOH solution. The organic layer was separated, dried over sodium sulfate and evaporated under reduced pressure to yield 69.2 mg of a colorless oil.

Example 3

Synthesis of (S)-(Me₂Val-Val-MeVal-Pro-pyrrolidin-2-yl)-methylketone (Compound I-1)

(a) Synthesis of (S)-Z-Val-Val-MeVal-Pro-pyrrolidin-2-yl) methylketone

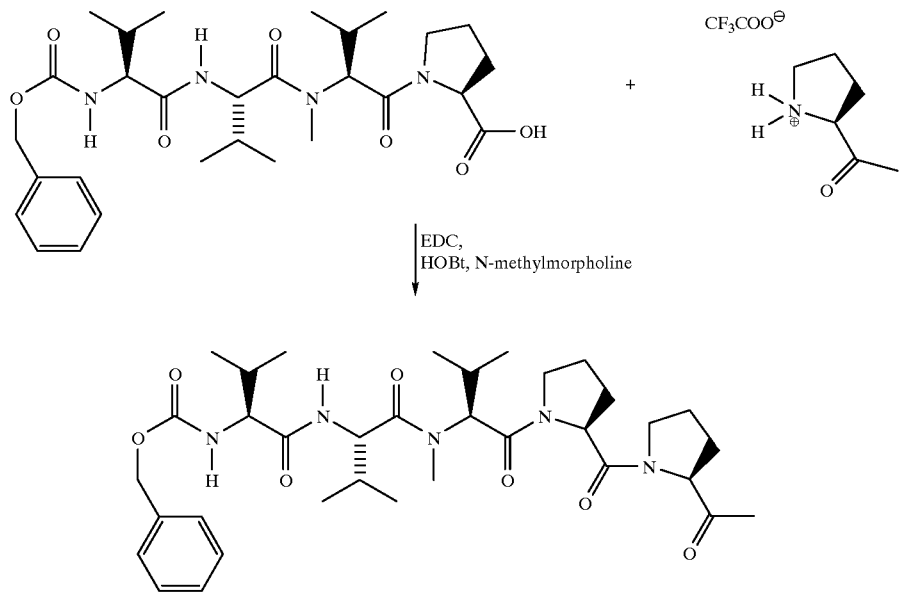

To a solution of 3.0 g Z-Val-Val-MeVal-Pro-OH and 0.89 g (S)-pyrrolidin-2-yl-methylketone trifluoroacetic acid salt in dichloromethane were added 1.03 g 1-ethyl-3-(3-dimethylaminopropyl)carbodiimide hydrochloride, 0.72 g N-hydroxybenzotriazol and 2.16 g N-methylmorpholine at 0° C. The mixture was stirred at room temperature overnight. The reaction mixture was then diluted with dichloromethane and washed sequentially with saturated aqueous sodium bicarbonate, a 5% aqueous solution of citric acid and brine. The organic phase was dried over sodium sulfate. Following filtration, the solvent was removed in vacuo. The residue was purified by silica gel chromatography (dichloromethane/isopropanol/triethyalmine 94:5:1) to provide 1.03 g ((S)-Z-Val-Val-MeVal-Pro-pyrrolidin-2-yl)-methylketone.

FAB-MS: 656.9 (M+H$^+$)

(b) Synthesis of (S)-(Me$_2$Val-Val-MeVal-Pro-pyrrolidin-2-yl)methylketone

To a solution of 1.03 g ((S)-Z-Val-Val-MeVal-Pro-pyrrolidin-2-yl)-methylketone in 150 ml methanol was added 38 mg palladium on charcoal (10l Pd by weight). The resulting suspension was hydrogenated at room temperature at atmospheric pressure for three hours. A 1.0 ml portion of an aqueous formaldehyde solution (37% by weight) and 0.226 g palladium on charcoal were added. The mixture was hydrogenated at room temperature at atmospheric pressure overnight. After filtration the solvent was removed in vacuo. The residue was purified by silica gel chromatography (ethyl acetate/isopropanol/triethyalmine 94:5:1) to provide 0.64 g (S)-(Me$_2$Val-Val-MeVal-Pro-pyrrolidin-2-yl)-methyl-ketone.

FAB-MS: 550.8 (M+H$^+$)

$^1$H-NMR (DMSO-d$_6$, 270 MHZ) δ=0.7 (m, 6 H), 0.8–1.0 (m, 12 H), 1.75–2.05 (m, 7 H), 2.0 (s, 3 H), 2.2 (s, 6 H), 2.6 (d, 1 H), 3.05 (s, 3 H), 3.55, (m, 1 H), 3.7 (m, 1 H), 4.35 (m, 1 H), 4.5–4.6 (m, 2 H), 4.95 (d, 1 H), 8.05 (d, 1 H) ppm Example 4

Synthesis of 2-[(S)-(Me$_2$Val-Val-MeVal-Pro-pyrorolidin-2-yl)]-5-phenyloxazole (Compound III-12)

NaOH and water. After drying with sodium sulfate, the solvent was removed under reduced pressure and the resulting crude material was purified by chromatography on silica gel.

Yield: 1.85 g. FAB-MS: 651 (M+H$^+$)

The following compounds were prepared via the methods disclosed above:

I-5 (S)-(Me$_2$Val-Val-MeVal-Pro-pyrrolidin-2-yl) butylketone FAB-MS: 592.5 (M+H$^+$)

I-12 (S)-(Me$_2$Val-Val-MeVal-Pro-pyrrolidin-2-yl)methoxymethylketone FAB-MS: 581 (M+H$^+$)

I-14 (S)-(Me$_2$Val-Val-MeVal-Pro-pyrrolidin-2-yl) benzylketone FAB-MS: 626 (M+H$^+$)

I-15 (S)-(Me$_2$Val-Val-MeVal-Pro-pyrrolidin-2-yl) phenylketone FAB-MS: 612 (M+H$^+$)

I-19 (S)-(Me$_2$Val-Val-MeVal-Pro-pyrrolidin-2-yl)-(4-trifluoromethylphenyl)-ketone FAB-MS: 680 (M+H$^+$)

I-20 (S)-(Me$_2$Val-Val-MeVal-Pro-pyrrolidin-2-yl)-(2-methoxyphenyl)-ketone FAB-MS: 642 (M+H$^+$)

I-22 (S)-(Me$_2$Val-Val-MeVal-Pro-pyrrolidin-2-yl)-(4-methoxyphenyl) ketone FAB-MS: 642.5 (M+H$^+$)

I-32 (S)-(Me$_2$Val-Val-MeVal-Pro-pyrrolidin-2-yl)-(4-fluorophenyl) ketone FAB-MS: 630.5 (M+H$^+$)

I-37 (S)-(Me$_2$Val-Val-MeVal-Pro-pyrrolidin-2-yl)-(2,4-bis(methoxy)phenyl)-ketone FAB-MS: 672 (M+H$^+$)

I-39 (S)-(Me$_2$Val-Val-MeVal-Pro-pyrrolidin-2-yl)-(3,4,5-tris(methoxy)phenyl)-ketone FAB-MS: 702 (M+H$^+$)

I-49 (S)-(Me2Val-Val-MeVal-Pro-pyrrolidin-2-yl)-(2-thiazolyl)-ketone FAB-MS: 619 (M+H$^+$)

I-54 (S)-(Me2Val-Val-MeVal-Pro-pyrrolidin-2-yl)-trifluoromethyl-ketone FAB-MS: 621.5 (M+H$_3$O$^+$)

I-63 Ethyl(S)-(Me$_2$Val-Val-MeVal-Pro-pyrrolidin-2-yl)-3-oxo-propionate FAB-MS: 622 (M+H$^+$)

I-79 N-Benzyl-(S)-(4)-(Me$_2$Val-Val-MeVal-Pro-pyrrolidin-2-yl)-4-oxo-butanoyl amide FAB-MS: 711 (M+H$^+$)

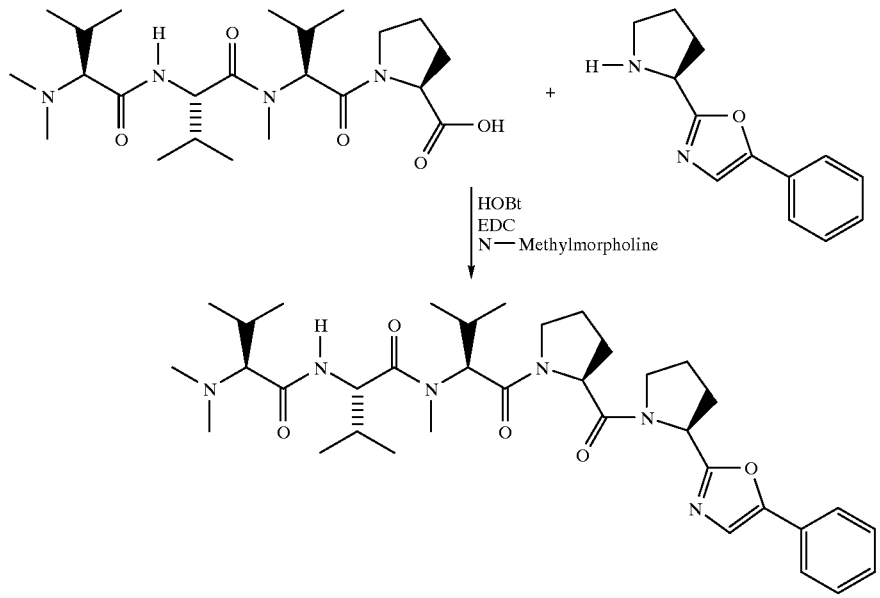

Me$_2$Val-Val-MeVal-Pro-OH (1.72 g, 3.8 mmol) and 2-(pyrrolidin-2-yl)-4-phenyl-oxazole (0.8 g, 3.8 mmol) were dissolved in 40 mL methylene chloride and the resulting solution was cooled to 0° C. HOBT.H$_2$O (0.5 g, 3.8 mmol) and EDC.HCl (0.7 g, 3.8 mmol) were then added, followed by NMM (0.5 mL, 4.5 mmol). After stirring overnight at room temperature, the reaction mixture was washed with 2N III-26 2-[(S)-(Me$_2$Val-Val-MeVal-Pro-pyrrolidin-2-yl)]-4-methyl-thiazole FAB-MS: 605 (M+H$^+$)

III-28 2-[(S)-(Me$_2$Val-Val-MeVal-Pro-pyrrolidin-2-yl)]-3,4-dimethyl-thiazole FAB-MS: 619 (M+H$^+$)

III-32 2-[(S)-(Me2Val-Val-MeVal-Pro-pyrrolidin-2-yl)]-5-tert.-butyl-thiazole FAB-MS: 647 (M+H$^+$)

III-35 2-[(S)-(Me$_2$Val-Val-MeVal-Pro-pyrrolidin-2-yl)]-4-phenyl-thiazole FAB-MS: 667 (M+H$^+$)

III-36 2-[(S)-(Me$_2$Val-Val-MeVal-Pro-pyrrolidin-2-yl)]-5-phenylthiazole FAB-MS: 667 (M+H$^+$)

III-46 2-[(S)-(Me$_2$Val-Val-MeVal-Pro-pyrrolidin-2-yl)]-4-carbonylethoxythiazole FAB-MS: 663 (M+H$^+$)

The compounds listed in Tables 1–8 below can be prepared using methods described above and the general methods for the synthesis of various building blocks outlined above as follows:

These compounds correspond to the indicated sequences:
Compounds I-1 to I-103: SEQ ID NO:3;
Compounds II-1 to II-103: SEQ ID NO:1;
Compounds III-1 to III-72; IV-1 to IV-72; V-1 to V-48; VI-1 to VI-48; VII-1 to VII-17; and VIII-1 to VIII-17; SEQ ID NO.:2.

Compounds I-1 to I-103 and II-1 to II-103: pyrrolidinyl ketones and piperidinyl ketones;

Compounds III-1 to III-24 and IV-1 to IV-24: pyrrolidinyl-oxazoles and piperidinyl-oxazoles;

Compounds III-25 to III-48 and IV-25 to IV-48: pyrrolidinyl-thiazoles and piperidinyl-thiazoles;

Compounds III-49 to III-72 and IV-49 to IV-72: pyrrolidinyl-imidazoles and piperidinyl-imidazoles;

Compounds V-1 to V-24 and VI-1 to VI-24: pyrrolidinyl-isoxazoles and piperidinyl-isoxazoles;

Compounds V-25 to V-48 and VI-25 to VI-48: pyrrolidinyl-pyrazoles and piperidinyl-pyrazoles;

Compounds VII-1 to VII-9 and VIII-1 to VIII-9: pyrrolidinyl-1,3,4-oxadiazoles and piperidinyl-1,3,4-oxadiazoles;

Compounds VII-10 to VII-17 and VIII-10 to VIII-17: pyrrolidinyl-1,3,4-thiadiazoles and piperidinyl-1,3,4-thiadiazoles.

TABLE 1

A is Me$_2$Val, B is Val, D is MeVal, E is Pro and F is of Formula II$_F$, a$_f$ is 1 and the —(C=O)-G group is in position 1 relative to the nitrogen atom in Formula II$_F$.

| No. | —C(=)-G |
|---|---|
| I-1 | —(C=O)—CH$_3$ |
| I-2 | —(C=O)—C$_2$H$_5$ |
| I-3 | —(C=O)-nC$_3$H$_7$ |
| I-4 | —(C=O)-isoC$_3$H$_7$ |
| I-6 | —(C=O)-tertC$_4$H$_9$ |
| I-7 | —(C=O)-cycloC$_3$H$_5$ |
| I-8 | —(C=O)-cycloC$_4$H$_7$ |
| I-9 | —(C=O)-cycloC$_5$H$_9$ |
| I-10 | —(C=O)-cycloC$_6$H$_{11}$ |
| I-11 | —(C=O)-cycloC$_7$H$_{12}$ |
| I-13 | —(C=O)—CH$_2$—CH$_2$—O—CH$_3$ |
| I-16 | —(C=O)—(4-HO—C$_6$H$_5$) |
| I-17 | —[(C=O)—(2-CF$_3$—C$_6$H$_4$] |
| I-18 | —[(C=O)—(3-CF$_3$—C$_6$H$_4$] |
| I-21 | —[(C=O)—(3-OCH$_3$—C$_6$H$_4$] |
| I-23 | —[(C=O)—(2-SCH$_3$—C$_6$H$_4$] |
| I-24 | —[(C=O)—(3-SCH$_3$—C$_6$H$_4$] |
| I-25 | —[(C=O)—(4-SCH$_3$—C$_6$H$_4$] |
| I-26 | —[(C=O)—(2-N(CH$_3$)$_2$—C$_6$H$_4$] |
| I-27 | —[(C=O)—(3-N(CH$_3$)$_2$—C$_6$H$_4$] |
| I-28 | —[(C=O)—(4-N(CH$_3$)$_2$—C$_6$H$_4$] |
| I-29 | —[(C=O)—(4-CN—C$_6$H$_4$] |
| I-30 | —[(C=O)—(4-Cl—C$_6$H$_4$] |
| I-31 | —[(C=O)—(4-Br—C$_6$H$_4$] |
| I-33 | —[(C=O)—(4-CH$_3$—C$_6$H$_4$] |
| I-34 | —[(C=O)—(2-NO$_2$—C$_6$H$_4$] |
| I-35 | —[(C=O)—(3-NO$_2$—C$_6$H$_4$] |
| I-36 | —[(C=O)—(4-NO$_2$—C$_6$H$_4$] |
| I-38 | —[(C=O)—(3,4-OCH$_3$—C$_6$H$_3$] |
| I-40 | —[(C=O)—(3,4-CH$_2$OCH$_2$—C$_6$H$_3$] |
| I-41 | —[(C=O)—(2,3-CH$_2$OCH$_2$—C$_6$H$_3$] |
| I-42 | —(C=O)-2-pyridinyl |
| I-43 | —(C=O)-2-furanyl |
| I-44 | —(C=O)-2-thienyl |
| I-45 | —(C=O) 3-pyridinyl |
| I-46 | —(C=O)-3-furanyl |
| I-47 | —(C=O)-3-thienyl |
| I-48 | —(C=O)-4-pyridinyl |
| I-50 | —(C=O)-2-oxazolyl |
| I-51 | —(C=O) 3-isoxazolyl |
| I-52 | —(C=O)-4-isoxazolyl |
| I-53 | —(C=O)-5-isoxazoyl |
| I-55 | —(C=O)—C$_2$F$_5$ |
| I-56 | —(C=O)—(C=O)—CH$_3$ |
| I-57 | —(C=O)—(C=O)—C$_2$H$_5$ |
| I-58 | —(C=O)—(C=O)-nC$_3$H$_7$ |
| I-59 | —(C=O)—(C=O)-tertC$_4$H$_9$ |
| I-60 | —(C=O)—(C=O)—CH$_2$—C$_6$H$_5$ |
| I-61 | —(C=O)—(C=O)—C$_6$H$_5$ |

TABLE 1-continued

A is Me$_2$Val, B is Val, D is MeVal, E is Pro and F is of Formula II$_f$, a$_f$ is 1 and the —(C=O)-G group is in position 1 relative to the nitrogen atom in Formula II$_f$.

| No. | —C(=)-G |
| --- | --- |
| I-62 | —(C=O)—CH$_2$—COOCH$_3$ |
| I-64 | —(C=O)—CF$_2$—COOCH$_3$ |
| I-65 | —(C=O)—CF$_2$—COOC$_2$H$_5$ |
| I-66 | —(C=O)—CH$_2$—CONH$_2$ |
| I-67 | —(C=O)—CH$_2$—CONHCH$_3$ |
| I-68 | —(C=O)—CH$_2$—CON(CH$_3$)$_2$ |
| I-69 | —(C=O)—CH$_2$—CONH—CH$_2$—C$_6$H$_5$ |
| I-70 | —(C=O)—CH$_2$—CONH—C$_6$H$_5$ |
| I-71 | —(C=O)—CH$_2$—CONH(CH$_2$—C$_6$H$_5$)$_2$ |
| I-72 | —(C=O)—CH$_2$—CON(—CH$_2$—CH$_2$—CH$_2$—CH$_2$—) |
| I-73 | —(C=O)—CH$_2$—CON(—CH$_2$CH$_2$—CH$_2$—CH$_2$—CH$_2$) |
| I-74 | —(C=O)—CH$_2$—CH$_2$—COOCH$_3$ |
| I-75 | —(C=O)—CH$_2$—CH$_2$—COOC$_2$H$_5$ |
| I-76 | —(C=O)—CH$_2$—CH$_2$—CONH$_2$ |
| I-77 | —(C=O)—CH$_2$—CH$_2$—CONHCH$_3$ |
| I-78 | —(C=O)—CH$_2$—CH$_2$—CON(CH$_3$)$_2$ |
| I-80 | —(C=O)—CH$_2$—CH$_2$—CONH—C$_6$H$_5$ |
| I-81 | —(C=O)—CH$_2$—CH$_2$—CONH(CH$_2$—C$_6$H$_5$)$_2$ |
| I-82 | —(C=O)—CH$_2$—CH$_2$—CON(—CH$_2$—CH$_2$—CH$_2$—CH$_2$—) |
| I-83 | —(C=O)—CH$_2$—CH$_2$—CON(—CH$_2$—CH$_2$—CH$_2$—CH$_2$—CH$_2$) |
| I-84 | —(C=O)—CH$_2$—COCH$_3$ |
| I-85 | —(C=O)—CH$_2$—CH$_2$—COCH$_3$ |
| I-86 | —(C=O)—CH$_2$—COC$_2$H$_5$ |
| I-87 | —(C=O)—CH$_2$—CH$_2$—COC$_2$H$_5$ |
| I-88 | —(C=O)—CH$_2$—CO—C$_6$H$_5$ |
| I-89 | —(C=O)—CH$_2$—CH$_2$—CO—C$_6$H$_5$ |
| I-90 | —(C=O)—CH$_2$—CO—CH$_2$—C$_6$H$_5$ |
| I-91 | —(C=O)—CH$_2$—CH$_2$—CO—CH$_2$—C$_6$H$_5$ |
| I-92 | —(C=O)—CH$_2$—SOC$_6$H$_5$ |
| I-93 | —(C=O)—CH$_2$—SOCH$_3$ |
| I-94 | —(C=O)—CH$_2$—SO(4-CH$_3$—C$_6$H$_4$) |
| I-95 | —(C=O)—CH$_2$—SO$_2$C$_6$H$_5$ |
| I-96 | —(C=O)—CH$_2$—SO$_2$CH$_3$ |
| I-97 | —(C=O)—CH$_2$—SO$_2$(4-CH$_3$—C$_6$H$_4$) |
| I-98 | —(C=O)—CH$_2$—CH$_2$—SOC$_6$H$_5$ |
| I-99 | —(C=O)—CH$_2$—CH$_2$—SOCH$_3$ |
| I-100 | —(C=O)—CH$_2$—CH$_2$—SO(4-CH$_3$—C$_6$H$_4$) |
| I-101 | —(C=O)—CH$_2$—CH$_2$—SO$_2$C$_6$H$_5$ |
| I-102 | —(C=O)—CH$_2$—CH$_2$—SO$_2$CH$_3$ |
| I-103 | —(C=O)—CH$_2$—CH$_2$—SO$_2$(4-CH$_3$—C$_6$H$_4$) |

TABLE 2

A is Me$_2$Val, B is Val, D is MeVal, E is Pro, F is of Formula II$_f$, a$_F$ is 2, and the —(C=O)-G group is in position 1 relative to the nitrogen atom in Formula II$_f$.

| No. | —C(=O)-G |
| --- | --- |
| II-1 | —(C=O)—CH$_3$ |
| II-2 | —(C=O)—C$_2$H$_5$ |
| II-3 | —(C=O)-nC$_3$H$_7$ |
| II-4 | —(C=O)-isoC$_3$H$_7$ |
| II-5 | —(C=O)-nC$_4$H$_9$ |
| II-6 | —(C=O)-tertC$_4$H$_9$ |
| II-7 | —(C=O)-cycloC$_3$H$_5$ |
| II-8 | —(C=O)-cycloC$_4$H$_7$ |
| II-9 | —(C=O)-cycloC$_5$H$_9$ |
| II-10 | —(C=O)-cycloC$_6$H$_{11}$ |
| II-11 | —(C=O)-cycloC$_7$H$_{12}$ |
| II-12 | —(C=O)—CH$_2$—O—CH$_3$ |
| II-13 | —(C=O)—CH$_2$—CH$_2$—O—CH$_3$ |
| II-14 | —(C=O)—CH$_2$—C$_6$H$_5$ |
| II-15 | —(C=O)—C$_6$H$_5$ |
| II-16 | —(C=O)—(4-HO—C$_6$H$_5$) |
| II-17 | —[(C=O)—(2-CF$_3$C$_6$H$_4$] |
| II-18 | —[(C=O)—(3-CF$_3$C$_6$H$_4$] |
| II-19 | —[(C=O)—(4-CF$_3$C$_6$H$_4$] |
| II-20 | —[(C=O)—(2-OCH$_3$—C$_6$H$_4$] |
| II-21 | —[(C=O)—(3-OCH$_3$—C$_6$H$_4$] |

TABLE 2-continued

A is Me$_2$Val, B is Val, D is MeVal, E is Pro, F
is of Formula II$_f$, a$_F$ is 2, and the —(C=O)-G group is in
position 1 relative to the nitrogen atom in Formula II$_f$.

| No. | —C(=O)-G |
|---|---|
| II-22 | —[(C=O)—(4-OCH$_3$—C$_6$H$_4$] |
| II-23 | —[(C=O)—(2-SCH$_3$—C$_6$H$_4$] |
| II-24 | —[(C=O)—(3-SCH$_3$—C$_6$H$_4$] |
| II-25 | —[(C=O)—(4-SCH$_3$—C$_6$H$_4$] |
| II-26 | —[(C=O)—(2-N(CH$_3$)$_2$—C$_6$H$_4$] |
| II-27 | —[(C=O)—(3-N(CH$_3$)$_2$—C$_6$H$_4$] |
| II-28 | —[(C=O)—(4-N(CH$_3$)$_2$—C$_6$H$_4$] |
| II-29 | —[(C=O)—(4-CN—C$_6$H$_4$] |
| II-30 | —[(C=O)—(4-Cl—C$_6$H$_4$] |
| II-31 | —[(C=O)—(4-Br—C$_6$H$_4$] |
| II-32 | —[(C=O)—(4-F-C$_6$H$_4$] |
| II-33 | —[(C=O)—(4-CH$_3$—C$_6$H$_4$] |
| II-34 | —[(C=O)—(2-NO$_2$—C$_6$H$_4$] |
| II-35 | —[(C=O)—(3-NO$_2$—C$_6$H$_4$] |
| II-36 | —[(C=O)—(4-NO$_2$—C$_6$H$_4$] |
| II-37 | —[(C=O)—(2,4-OCH$_3$—C$_6$H$_3$] |
| II-38 | —[(C=O)—(3,4-OCH$_3$—C$_6$H$_3$] |
| II-39 | —[(C=O)—(3,4,5-OCH$_3$—C$_6$H$_2$] |
| II-40 | —[(C=O)—(3,4-CH$_2$OCH$_2$—C$_6$H$_3$] |
| II-41 | —[(C=O)—(2,3-CH$_2$OCH$_3$—C$_6$H$_3$] |
| II-42 | —(C=O)-2-pyridinyl |
| II-43 | —(C=O)-2-furanyl |
| II-44 | —(C=O)-2-thienyl |
| II-45 | —(C=O)-3-pyridinyl |
| II-46 | —(C=O)-3-furanyl |
| II-47 | —(C=O)-3-thienyl |
| II-48 | —(C=O)-4-pyridinyl |
| II-49 | —(C=O)-2-thiazolyl |
| II-50 | —(C=O)-2-oxazolyl |
| II-51 | —(C=O)-3-isoxazolyl |
| II-52 | —(C=O)-4-isoxazolyl |
| II-53 | —(C=O)-5-isoxazoyl |
| II-54 | —(C=O)—CF$_3$ |
| II-55 | —(C=O)—C$_2$F$_5$ |
| II-56 | —(C=O)—(C=O)—CH$_3$ |
| II-57 | —(C=O)—(C=O)—C$_2$H$_5$ |
| II-58 | —(C=O)—(C=O)-nC$_3$H$_7$ |
| II-59 | —(C=O)—(C=O)-tertC$_4$H$_9$ |
| II-60 | —(C=C)—(C=O)—CH$_2$—C$_6$H$_5$ |
| II-61 | —(C=O)—(C=O)—C$_6$H$_5$ |
| II-62 | —(C=O)—CH$_2$—COOCH$_3$ |
| II-63 | —(C=O)—CH$_2$—COOC$_2$H$_5$ |
| II-64 | —(C=O)—CF$_2$—COOCH$_3$ |
| II-65 | —(C=O)—CF$_2$—COOC$_2$H$_5$ |
| II-66 | —(C=O)—CH$_2$—CONH$_2$ |
| II-67 | —(C=O)—CH$_2$—CONHCH$_3$ |
| II-68 | —(C=O)—CH$_2$—CON(CH$_3$)$_2$ |
| II-69 | —(C=O)—CH$_2$—CONH—CH$_2$—C$_6$H$_5$ |
| II-70 | —(C=O)—CH$_2$—CONH—C$_6$H$_5$ |
| II-71 | —(C=O)—CH$_2$—CONH(CH$_2$—C$_6$H$_5$)$_2$ |
| II-72 | —(C=O)—CH$_2$—CON(—CH$_2$—CH$_2$—CH$_2$—CH$_2$—) |
| II-73 | —(C=O)—CH$_2$—CON(—CH$_2$—CH$_2$—CH$_2$—CH$_2$—CH$_2$) |
| II-74 | —(C=O)—CH$_2$—CH$_2$—COOCH$_3$ |
| II-75 | —(C=O)—CH$_2$—CH$_2$—COOC$_2$H$_5$ |
| II-76 | —(C=O)—CH$_2$—CH$_2$—CONH$_2$ |
| II-77 | —(C=O)—CH$_2$—CH$_2$—CONHCH$_3$ |
| II-78 | —(C=O)—CH$_2$—CH$_2$—CON(CH$_3$)$_2$ |
| II-79 | —(C=O)—CH$_2$—CH$_2$—CONH—CH$_2$—C$_6$H$_5$ |
| II-80 | —(C=O)—CH$_2$—CH$_2$—CONH—C$_6$H$_5$ |
| II-81 | —(C=O)—CH$_2$—CH$_2$—CONH(CH$_2$—C$_6$H$_5$)$_2$ |
| II-82 | —(C=O)—CH$_2$—CH$_2$—CON(—CH$_2$—CH$_2$—CH$_2$—CH$_2$—) |
| II-83 | —(C=O)—CH$_2$—CH$_2$—CON(—CH$_2$—CH$_2$—CH$_2$—CH$_2$—CH$_2$) |
| II-84 | —(C=O)—CH$_2$—COCH$_3$ |
| II-85 | —(C=O)—CH$_2$—CH$_2$—COCH$_3$ |
| II-86 | —(C=O)—CH$_2$—COC$_2$H$_5$ |
| II-87 | —(C=O)—CH$_2$—CH$_2$—COC$_2$H$_5$ |
| II-88 | —(C=O)—CH$_2$—CO—C$_6$H$_5$ |
| II-89 | —(C=O)—CH$_2$—CH$_2$—CO—C$_6$H$_5$ |
| II-90 | —(C=O)—CH$_2$—CO—CH$_2$—C$_6$H$_5$ |
| II-91 | —(C=O)—CH$_2$—CH$_2$—CO—CH$_2$—C$_6$H$_5$ |
| II-92 | —(C=O)—CH$_2$—SOC$_6$H$_5$ |
| II-93 | —(C=O)—CH$_2$—SOCH$_3$ |
| II-94 | —(C=O)—CH$_2$—SO(4-CH$_3$—C$_6$H$_4$) |

TABLE 2-continued

A is Me$_2$Val, B is Val, D is MeVal, E is Pro, F is of Formula II$_f$, a$_F$ is 2, and the —(C=O)-G group is in position 1 relative to the nitrogen atom in Formula II$_f$.

| No. | —C(=O)-G |
|---|---|
| II-95 | —(C=O)—CH$_2$—SO$_2$C$_6$H$_5$ |
| II-96 | —(C=O)—CH$_2$—SO$_2$CH$_3$ |
| II-97 | —(C=O)—CH$_2$—SO$_2$(4-CH$_3$—C$_6$H$_4$) |
| II-98 | —(C=O)—CH$_2$—CH$_2$—SOC$_6$H$_5$ |
| II-99 | —(C=O)—CH$_2$—CH$_2$—SOCH$_3$ |
| II-100 | —(C=O)—CH$_2$—CH$_2$—SO(4-CH$_3$—C$_6$H$_4$) |
| II-101 | —(C=O)—CH$_2$—CH$_2$—SO$_2$C$_6$H$_5$ |
| II-102 | —(C=O)—CH$_2$—CH$_2$—SO$_2$CH$_3$ |
| II-103 | —(C=O)—CH$_2$—CH$_2$—SO$_2$(4-CH$_3$—C$_6$H$_4$) |

TABLE 3

A is Me$_2$Val, B is Val, D is MeVal, E is Pro, F is of Formula III$_f$, G is of Formula VII$_g$, b$_f$ = 1, and G is in position 1 relative to the nitrogen atom in Formula III$_f$.

| No. | X | R$^7_1$ | R$^8_1$ |
|---|---|---|---|
| III-1 | O | H | H |
| III-2 | O | H | CH$_3$ |
| III-3 | O | CH$_3$ | H |
| III-4 | O | CH$_3$ | CH$_3$ |
| III-5 | O | H | C$_2$H$_5$ |
| III-6 | O | C$_2$H$_5$ | H |
| III-7 | O | C$_2$H$_5$ | C$_2$H$_5$ |
| III-8 | O | H | t-C$_4$H$_9$ |
| III-9 | O | t-C$_4$H$_9$ | H |
| III-10 | O | t-C$_4$H$_9$ | t-C$_4$H$_9$ |
| III-11 | O | H | C$_6$H$_5$ |
| III-12 | O | C$_6$H$_5$ | H |
| III-13 | O | C$_6$H$_5$ | CH$_3$ |
| III-14 | O | CH$_3$ | C$_6$H$_5$ |
| III-15 | O | C$_6$H$_5$ | C$_6$H$_5$ |
| III-16 | O | H | CH$_2$—C$_6$H$_5$ |
| III-17 | O | CH$_2$—C$_6$H$_5$ | H |
| III-18 | O | CH$_2$—C$_6$H$_5$ | CH$_2$—C$_6$H$_5$ |
| III-19 | O | H | COOCH$_3$ |
| III-20 | O | COOCH$_3$ | H |
| III-21 | O | COOCH$_3$ | COOCH$_3$ |
| III-22 | O | H | COOC$_2$H$_5$ |
| III-23 | O | COOC$_2$H$_5$ | H |
| III-24 | O | COOC$_2$H$_5$ | COOC$_2$H$_5$ |
| III-25 | S | H | H |
| III-27 | S | CH$_3$ | H |
| III-29 | S | H | C$_2$H$_5$ |
| III-30 | S | C$_2$H$_5$ | H |
| III-31 | S | C$_2$H$_5$ | C$_2$H$_5$ |
| III-33 | S | t-C$_4$H$_9$ | H |
| III-34 | S | t-C$_4$H$_9$ | t-C$_4$H$_9$ |
| III-37 | S | C$_6$H$_5$ | CH$_3$ |
| III-38 | S | CH$_3$ | C$_6$H$_5$ |
| III-39 | S | C$_6$H$_5$ | C$_6$H$_5$ |
| III-40 | S | H | CH$_2$—C$_6$H$_5$ |
| III-41 | S | CH$_2$—C$_6$H$_5$ | H |
| III-42 | S | CH$_2$—C$_6$H$_5$ | CH$_2$—C$_6$H$_5$ |
| III-43 | S | H | COOCH$_3$ |
| III-44 | S | COOCH$_3$ | H |
| III-45 | S | COOCH$_3$ | COOCH$_3$ |
| III-47 | S | COOC$_2$H$_5$ | H |
| III-48 | S | COOC$_2$H$_5$ | COOC$_2$H$_5$ |
| III-49 | NH | H | H |
| III-50 | NH | H | CH$_3$ |
| III-51 | NH | CH$_3$ | H |
| III-52 | NH | CH$_3$ | CH$_3$ |
| III-53 | NH | H | C$_2$H$_5$ |
| III-54 | NH | C$_2$H$_5$ | H |
| III-55 | NH | C$_2$H$_5$ | C$_2$H$_5$ |
| III-56 | NH | H | t-C$_4$H$_9$ |
| III-57 | NH | t-C$_4$H$_9$ | H |
| III-58 | NH | t-C$_4$H$_9$ | t-C$_4$H$_9$ |
| III-59 | NH | H | C$_6$H$_5$ |
| III-60 | NH | C$_6$H$_5$ | H |
| III-61 | NH | C$_6$H$_5$ | CH$_3$ |
| III-62 | NH | CH$_3$ | C$_6$H$_5$ |
| III-63 | NH | C$_6$H$_5$ | C$_6$H$_5$ |
| III-64 | NH | H | CH$_2$—C$_6$H$_5$ |
| III-65 | NH | CH$_2$—C$_6$H$_5$ | H |
| III-66 | NH | CH$_2$—C$_6$H$_5$ | CH$_2$—C$_6$H$_5$ |
| III-67 | NH | H | COOCH$_3$ |
| III-68 | NH | COOCH$_3$ | H |
| III-69 | NH | COOCH$_3$ | COOCH$_3$ |
| III-70 | NH | H | COOC$_2$H$_5$ |
| III-71 | NH | COOC$_2$H$_5$ | H |
| III-72 | NH | COOC$_2$H$_5$ | COOC$_2$H$_5$ |

TABLE 4

A is Me$_2$Val, B is Val, D is MeVal, E is Pro, F is of Formula III$_f$, G is of Formula VII$_g$, b$_f$ = 2, and G is in position 1 relative to the nitrogen atom in Formula III$_f$.

| No. | X | R$^7_1$ | R$^8_1$ |
|---|---|---|---|
| IV-1 | O | H | H |
| IV-2 | O | H | CH$_3$ |
| IV-3 | O | CH$_3$ | H |
| IV-4 | O | CH$_3$ | CH$_3$ |
| IV-5 | C | H | C$_2$H$_5$ |
| IV-6 | O | C$_2$H$_5$ | H |
| IV-7 | C | C$_2$H$_5$ | C$_2$H$_5$ |
| IV-8 | O | H | t-C$_4$H$_9$ |
| IV-9 | O | t-C$_4$H$_9$ | H |
| IV-10 | O | t-C$_4$H$_9$ | t-C$_4$H$_9$ |
| IV-11 | C | H | C$_6$H$_5$ |
| IV-12 | O | C$_6$H$_5$ | H |
| IV-13 | O | C$_6$H$_5$ | CH$_3$ |
| IV-14 | O | CH$_3$ | C$_6$H$_5$ |
| IV-15 | O | C$_6$H$_5$ | C$_6$H$_5$ |
| IV-16 | O | H | CH$_2$—C$_6$H$_5$ |
| IV-17 | O | CH$_2$—C$_6$H$_5$ | H |
| IV-18 | O | CH$_2$—C$_6$H$_5$ | CH$_2$—C$_6$H$_5$ |
| IV-19 | O | H | COOCH$_3$ |
| IV-20 | O | COOCH$_3$ | H |
| IV-21 | O | COOCH$_3$ | COOCH$_3$ |
| IV-22 | O | H | COOC$_2$H$_5$ |
| IV-23 | O | COOC$_2$H$_5$ | H |
| IV-24 | C | COOC$_2$H$_5$ | COOC$_2$H$_5$ |
| IV-25 | S | H | H |

TABLE 4-continued

A is Me$_2$Val, B is Val, D is MeVal, E is Pro, F is of Formula III$_f$, G is of Formula VII$_g$, b$_f$ = 2, and G is in position 1 relative to the nitrogen atom in Formula III$_f$.

| No. | X | R$^7{}_1$ | R$^8{}_1$ |
|---|---|---|---|
| IV-26 | S | H | CH$_3$ |
| IV-27 | S | CH$_3$ | H |
| IV-28 | S | CH$_3$ | CH$_3$ |
| IV-29 | S | H | C$_2$H$_5$ |
| IV-30 | S | C$_2$H$_5$ | H |
| IV-31 | S | C$_2$H$_5$ | C$_2$H$_5$ |
| IV-32 | S | H | t-C$_4$H$_9$ |
| IV-33 | S | t-C$_4$H$_9$ | H |
| IV-34 | S | t-C$_4$H$_9$ | t-C$_4$H$_9$ |
| IV-35 | S | H | C$_6$H$_5$ |
| IV-36 | S | C$_6$H$_5$ | H |
| IV-37 | S | C$_6$H$_5$ | CH$_3$ |
| IV-38 | S | CH$_3$ | C$_6$H$_5$ |
| IV-39 | S | C$_6$H$_5$ | C$_6$H$_5$ |
| IV-40 | S | H | CH$_2$—C$_6$H$_5$ |
| IV-41 | S | CH$_2$—C$_6$H$_5$ | H |
| IV-42 | S | CH$_2$—C$_6$H$_5$ | CH$_2$—C$_6$H$_5$ |
| IV-43 | S | H | COOCH$_3$ |
| IV-44 | S | COOCH$_3$ | H |
| IV-45 | S | COOCH$_3$ | COOCH$_3$ |
| IV-46 | S | H | COOC$_2$H$_5$ |
| IV-47 | S | COOC$_2$H$_5$ | H |
| IV-48 | S | COOC$_2$H$_5$ | COOC$_2$H$_5$ |
| IV-49 | NH | H | H |
| IV-50 | NH | H | CH$_3$ |
| IV-51 | NH | CH$_3$ | H |
| IV-52 | NH | CH$_3$ | CH$_3$ |
| IV-53 | NH | H | C$_2$H$_5$ |
| IV-54 | NH | C$_2$H$_5$ | H |
| IV-55 | NH | C$_2$H$_5$ | C$_2$H$_5$ |
| IV-56 | NH | H | t-C$_4$H$_9$ |
| IV-57 | NH | t-C$_4$H$_9$ | H |
| IV-58 | NH | t-C$_4$H$_9$ | t-C$_4$H$_9$ |
| IV-59 | NH | H | C$_6$H$_5$ |
| IV-60 | NH | C$_6$H$_5$ | H |
| IV-61 | NH | C$_6$H$_5$ | CH$_3$ |
| IV-62 | NH | CH$_3$ | C$_6$H$_5$ |
| IV-63 | NH | C$_6$H$_5$ | C$_6$H$_5$ |
| IV-64 | NH | H | CH$_2$—C$_6$H$_5$ |
| IV-65 | NH | CH$_2$—C$_6$H$_5$ | H |
| IV-66 | NH | CH$_2$—C$_6$H$_5$ | CH$_2$—C$_6$H$_5$ |
| IV-67 | NH | H | COOCH$_3$ |
| IV-68 | NH | COOCH$_3$ | H |
| IV-69 | NH | COOCH$_3$ | COOCH$_3$ |
| IV-70 | NH | H | COOC$_2$H$_5$ |
| IV-71 | NH | COOC$_2$H$_5$ | H |
| IV-72 | NH | COOC$_2$H$_5$ | COOC$_2$H$_5$ |

TABLE 5

A is Me$_2$Val, B is Val, D is MeVal, E is Pro, F is of Formula III$_f$, G is of Formula VIII$_g$, b$_f$ = 1, and G is in position 1 relative to the nitrogen atom in Formula III$_f$.

| No. | X | R$^{10}{}_1$ | R$^{11}{}_1$ |
|---|---|---|---|
| V-1 | O | H | H |
| V-2 | O | H | CH$_3$ |
| V-3 | O | CH$_3$ | H |
| V-4 | O | CH$_3$ | CH$_3$ |
| V-5 | O | H | C$_2$H$_5$ |
| V-6 | O | C$_2$H$_5$ | H |
| V-7 | O | C$_2$H$_5$ | C$_2$H$_5$ |
| V-8 | O | H | t-C$_4$H$_9$ |
| V-9 | O | t-C$_4$H$_9$ | H |
| V-10 | O | t-C$_4$H$_9$ | t-C$_4$H$_9$ |
| V-11 | O | H | C$_6$H$_5$ |
| V-12 | O | C$_6$H$_5$ | H |
| V-13 | O | C$_6$H$_5$ | CH$_3$ |
| V-14 | O | CH$_3$ | C$_6$H$_5$ |
| V-15 | O | C$_6$H$_5$ | C$_6$H$_5$ |
| V-16 | O | H | CH$_2$—C$_6$H$_5$ |
| V-17 | O | CH$_2$—C$_6$H$_5$ | H |
| V-18 | O | CH$_2$—C$_6$H$_5$ | CH$_2$—C$_6$H$_5$ |
| V-19 | O | H | COOCH$_3$ |
| V-20 | O | COOCH$_3$ | H |
| V-21 | O | COOCH$_3$ | COOCH$_3$ |
| V-22 | O | H | COOC$_2$H$_5$ |
| V-23 | O | COOC$_2$H$_5$ | H |
| V-24 | O | COOC$_2$H$_5$ | COOC$_2$H$_5$ |
| V-25 | NH | H | H |
| V-26 | NH | H | CH$_3$ |
| V-27 | NH | CH$_3$ | H |
| V-28 | NH | CH$_3$ | CH$_3$ |
| V-29 | NH | H | C$_2$H$_5$ |
| V-30 | NH | C$_2$H$_5$ | H |
| V-31 | NH | C$_2$H$_5$ | C$_2$H$_5$ |
| V-32 | NH | H | t-C$_4$H$_9$ |
| V-33 | NH | t-C$_4$H$_9$ | H |
| V-34 | NH | t-C$_4$H$_9$ | t-C$_4$H$_9$ |
| V-35 | NH | H | C$_6$H$_5$ |
| V-36 | NH | C$_6$H$_5$ | H |
| V-37 | NH | C$_6$H$_5$ | CH$_3$ |
| V-38 | NH | CH$_3$ | C$_6$H$_5$ |
| V-39 | NH | C$_6$H$_5$ | C$_6$H$_5$ |
| V-40 | NH | H | CH$_2$—C$_6$H$_5$ |
| V-41 | NH | CH$_2$—C$_6$H$_5$ | H |
| V-42 | NH | CH$_2$—C$_6$H$_5$ | CH$_2$—C$_6$H$_5$ |
| V-43 | NH | H | COOCH$_3$ |
| V-44 | NH | COOCH$_3$ | H |
| V-45 | NH | COOCH$_3$ | COOCH$_3$ |
| V-46 | NH | H | COOC$_2$H$_5$ |
| V-47 | NH | COOC$_2$H$_5$ | H |
| V-48 | NH | COOC$_2$H$_5$ | COOC$_2$H$_5$ |

TABLE 6

A is Me$_2$Val, B is Val, D is MeVal, E is Pro, F is of Formula III$_f$, G is of Formula VIII$_g$, b$_f$ = 2, and G is in position 1 relative to the nitrogen atom in Formula III$_f$.

| No. | X | R$^{10}{}_1$ | R$^{11}{}_1$ |
|---|---|---|---|
| VI-1 | O | H | H |
| VI-2 | O | H | CH$_3$ |
| VI-3 | O | CH$_3$ | H |
| VI-4 | O | CH$_3$ | CH$_3$ |
| VI-5 | O | H | C$_2$H$_5$ |
| VI-6 | O | C$_2$H$_5$ | H |
| VI-7 | O | C$_2$H$_5$ | C$_2$H$_5$ |
| VI-8 | O | H | t-C$_4$H$_9$ |
| VI-9 | O | t-C$_4$H$_9$ | H |
| VI-10 | O | t-C$_4$H$_9$ | t-C$_4$H$_9$ |
| VI-11 | O | H | C$_6$H$_5$ |
| VI-12 | O | C$_6$H$_5$ | H |
| VI-13 | O | C$_6$H$_5$ | CH$_3$ |
| VI-14 | O | CH$_3$ | C$_6$H$_5$ |
| VI-15 | O | C$_6$H$_5$ | C$_6$H$_5$ |
| VI-16 | O | H | CH$_2$—C$_6$H$_5$ |
| VI-17 | O | CH$_2$—C$_6$H$_5$ | H |
| VI-18 | O | CH$_2$—C$_6$H$_5$ | CH$_2$—C$_6$H$_5$ |
| VI-19 | O | H | COOCH$_3$ |
| VI-20 | O | COOCH$_3$ | H |
| VI-21 | O | COOCH$_3$ | COOCH$_3$ |
| VI-22 | O | H | COOC$_2$H$_5$ |
| VI-23 | O | COOC$_2$H$_5$ | H |
| VI-24 | O | COOC$_2$H$_5$ | COOC$_2$H$_5$ |
| VI-25 | NH | H | H |
| VI-26 | NH | H | CH$_3$ |
| VI-27 | NH | CH$_3$ | H |

TABLE 6-continued

A is Me$_2$Val, B is Val, D is MeVal, E is Pro, F is of Formula III$_f$, G is of Formula VIII$_g$, b$_f$ = 2, and G is in position 1 relative to the nitrogen atom in Formula III$_f$.

| No. | X | R$^{10}_1$ | R$^{11}_1$ |
|---|---|---|---|
| VI-28 | NH | CH$_3$ | CH$_3$ |
| VI-29 | NH | H | C$_2$H$_5$ |
| VI-30 | NH | C$_2$H$_5$ | H |
| VI-31 | NH | C$_2$H$_5$ | C$_2$H$_5$ |
| VI-32 | NH | H | t-C$_4$H$_9$ |
| VI-33 | NH | t-C$_4$H$_9$ | H |
| VI-34 | NH | t-C$_4$H$_9$ | t-C$_4$H$_9$ |
| VI-35 | NH | H | C$_6$H$_5$ |
| VI-36 | NH | C$_6$H$_5$ | H |
| VI-37 | NH | C$_6$H$_5$ | CH$_3$ |
| VI-38 | NH | CH$_3$ | C$_6$H$_5$ |
| VI-39 | NH | C$_6$H$_5$ | C$_6$H$_5$ |
| VI-40 | NH | H | CH$_2$—C$_6$H$_5$ |
| VI-41 | NH | CH$_2$—C$_6$H$_5$ | H |
| VI-42 | NH | CH$_2$—C$_6$H$_5$ | CH$_2$—C$_6$H$_5$ |
| VI-43 | NH | H | COOCH$_3$ |
| VI-44 | NH | COOCH$_3$ | H |
| VI-45 | NH | COOCH$_3$ | COOCH$_3$ |
| VI-46 | NH | H | COOC$_2$H$_5$ |
| VI-47 | NH | COOC$_2$H$_5$ | H |
| VI-48 | NH | COOC$_2$H$_5$ | COOC$_2$H$_5$ |

TABLE 7

A is Me$_2$Val, B is Val, D is MeVal, E is Pro, F is of Formula III$_f$, G is of Formula IX$_g$, b$_f$ = 1, and G is in position 1 relative to the nitrogen atom in Formula III$_f$.

| No. | X | R$^{13}_1$ |
|---|---|---|
| VII-1 | O | H |
| VII-2 | O | CH$_3$ |
| VII-3 | O | C$_2$H$_5$ |
| VII-4 | O | C$_3$H$_7$ |
| VII-5 | O | t-C$_4$H$_9$ |
| VII-6 | O | COOCH$_3$ |
| VII-7 | O | COOC$_2$H$_5$ |
| VII-8 | O | C$_6$H$_5$ |
| VII-9 | O | CH$_2$—C$_6$H$_5$ |
| VII-10 | S | CH$_3$ |
| VII-11 | S | C$_2$H$_5$ |
| VII-12 | S | C$_3$H$_7$ |
| VII-13 | S | t-C$_4$H$_9$ |
| VII-14 | S | COOCH$_3$ |
| VII-15 | S | COOC$_2$H$_5$ |
| VII-16 | S | C$_6$H$_5$ |
| VII-17 | S | CH$_2$—C$_6$H$_5$ |

TABLE 8

A is Me$_2$Val, B is Val, D is MeVal, E is Pro, F is of Formula III$_f$, G is of Formula IX$_g$, b$_f$ = 2, and G is in position 1 relative to the nitrogen atom in Formula III$_f$.

| No. | X | R$^{13}_1$ |
|---|---|---|
| VIII-1 | O | H |
| VIII-2 | O | CH$_3$ |
| VIII-3 | O | C$_2$H$_5$ |
| VIII-4 | O | C$_3$H$_7$ |
| VIII-5 | O | t-C$_4$H$_9$ |
| VIII-6 | O | COOCH$_3$ |
| VIII-7 | O | COOC$_2$H$_5$ |
| VIII-8 | O | C$_6$H$_5$ |
| VIII-9 | O | CH$_2$—C$_6$H$_5$ |
| VIII-10 | S | CH$_3$ |
| VIII-11 | S | C$_2$H$_5$ |
| VIII-12 | S | C$_3$H$_7$ |
| VIII-13 | S | t-C$_4$H$_9$ |
| VIII-14 | S | COOCH$_3$ |
| VIII-15 | S | COOC$_2$H$_5$ |
| VIII-16 | S | C$_6$H$_5$ |
| VIII-17 | S | CH$_2$—C$_6$H$_5$ |

Evaluation of Biological Activity

In vitro methodology

Cytotoxicity was measured using standard methodology for adherent cell lines, such as the microculture tetrazolium assay (MTT). Details of this assay have been published (Alley, M. C., et al., *Cancer Research*, 48: 589–601,(1988)). Exponentially growing cultures of HT-29 colon carcinoma cells were used to make microtiter plate cultures. Cells were seeded at 5000–20,000 cells per well in 96-well plates (in 150 ml of media), and grown overnight at 37° C. Test compounds were added, in 10-fold dilutions varying from $10^{-4}$M to $10^{-10}$M. Cells were then incubated for 48 hours. To determine the number of viable cells in each well, the MTT dye was added (50 ml of a 3 mg/ml solution of 3-(4,5-dimethylthiazol-2-yl)-2,5-diphenyltetrazolium bromide in saline). This mixture was incubated at 37° C. for 5 hours, and then 50 ml of 25% SDS, pH 2, was added to each well. After an overnight incubation, the absorbance of each well at 550 nm was read using an ELISA reader. The values for the mean ±SD of data from replicated wells were calculated, using the formula % T/C (% viable cells treated/control). The concentration of test compound which gives a T/C of 50% growth inhibition was designated as the IC$_{50}$.

Table 9, below, presents the IC$_{50}$ values determined in the HT-29 cell system:

TABLE 9

| Compound No. | IC$_{50}$ (mol/L) |
|---|---|
| I-1 | >10$^{-6}$ |
| I-5 | >10$^{-6}$ |
| I-12 | 4 × 10$^{-7}$ |
| I-14 | 4 × 10$^{-7}$ |
| I-15 | 1.7 × 10$^{-6}$ |
| I-19 | >10$^{-6}$ |
| I-20 | 2.8 × 10$^{-7}$ |
| I-22 | >10$^{-6}$ |
| I-32 | >10$^{-6}$ |
| I-37 | 3 × 10$^{-7}$ |
| I-39 | >10$^{-6}$ |
| I-49 | >10$^{-6}$ |
| I-54 | >10$^{-6}$ |
| I-63 | 4 × 10$^{-8}$ |
| III-12 | 9 × 10$^{-7}$ |
| III-26 | >10$^{-6}$ |
| III-28 | 4 × 10$^{-7}$ |
| III-32 | >10$^{-6}$ |
| III-35 | >10$^{-6}$ |
| III-36 | 4 × 10$^{-7}$ |
| III-46 | 6 × 10$^{-7}$ |
| V-2 | 3 × 10$^{-6}$ |

In vivo methodology

Compounds of this invention may be further tested in any of the various preclinical assays for in vivo activity which are indicative of clinical utility. Such assays are conducted with nude mice into which tumor tissue, preferably of human origin, has been transplanted ("xenografted"), as is well known in this field. Test compounds are evaluated for their anti-tumor efficacy following administration to the xenograft-bearing mice.

Compound I-15, listed above, was tested in the P388 murine lymphocytic leukemia screening model. P388 celss were harvested from donor mice by peritoneal lavage at day 7 post-transplant and the drugs were administered intravenously for 5 consecutive days. The survival period for untreated mice was in the range of 11 to 13 days. The data are shown in Table 9 below, and are expressed as mean survival time (MST and the increase in lifespan relative to the control as T/C% (treated/control%). According to National Cancer Institute guidelines, a T/C% in the range of 128–190% indicates a drug with moderate to good activity.

TABLE 10

Activity of Compound I-15 against P388 murine leukemia.

| Dose (mg/kg) | MST (days) | T/C% |
|---|---|---|
| 0 | 11 | 100 |
| 50 | 15 | 136 |
| 60 | 16 | 145 |
| 75 | 17 | 155 |

In addition, human tumors which have been grown in athymic nude mice can be transplanted into new recipient animals, using tumor fragments which are about 50 mg in size. The day of transplantation is designated as day 0. Six to ten days later, the mice are treated with the test compounds given as an intravenous or intraperitoneal injection, in groups of 5–10 mice at each dose. Compounds are given daily for 5 days, 10 days or 15 days, at doses from 10–100 mg/kg body weight. Tumor diameters and body weights are measured twice weekly. Tumor masses are calculated using the diameters measured with Vernier calipers, and the formula:

$$(\text{length} \times \text{width}^2)/2 = \text{mg of tumor weight}$$

Mean tumor weights are calculated for each treatment group, and T/C values determined for each group relative to the untreated control tumors.

Equivalents

Those skilled in the art will recognize or be able to ascertain using no more than routine experimentation many equivalents to the specific embodiments of the invention described herein. Such equivalents are intended to be encompassed in the scope of the following claims.

We claim:

1. A compound of the formula

A-B-D-E-F-G, or a salt thereof with a pharmaceutically acceptable acid, wherein

A is α-amino acid residue of Formula $II_a$,

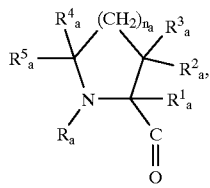

(II$_a$)

wherein $n_a$ is 0 to 3; $R_a$ is hydrogen, or unsubstituted or fluorine-substituted normal, branched or cyclic $C_1$–$C_3$-alkyl; $R^1_a$ is hydrogen, $C_1$–$C_3$-alkyl, phenyl, or substituted phenyl; or $R_a$ and $R^1_a$ together form a propylene bridge; and $R^2_a$, $R^3_a$, $R^4_a$ and $R^5_a$ are each, independently, hydrogen or alkyl; or an α-amino acid residue of Formula $III_a$,

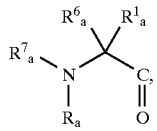

(III$_a$)

wherein $R_a$ is hydrogen or unsubstituted or fluorine-substituted $C_1$–$C_3$-alkyl; $R^1_a$ is hydrogen or $C_1$–$C_4$-alkyl; $R^6_a$ is alkyl, substituted alkyl, alkenyl, phenyl or substituted phenyl; or $R^1_a$ is an alkyl group and $R^6_a$ is $C_1$–$C_6$-alkyl, cycloalkylmethyl, benzyl or substituted benzyl; and $R^7_a$ is hydrogen or alkyl; or an α-amino acid residue of Formula $IV_a$,

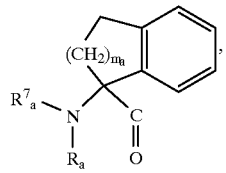

(IV$_a$)

wherein $m_a$ is 1 or 2; $R^7_a$ is hydrogen or alkyl; $R_a$ is hydrogen, or unsubstituted or fluorine-substituted alkyl; or an α-amino acid residue of Formula $V_a$,

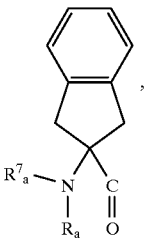

(V$_a$)

wherein $R^7_a$ is hydrogen or alkyl and $R_a$ is hydrogen, or unsubstituted or fluorine-substituted alkyl; or an α-amino acid of Formula $VI_a$,

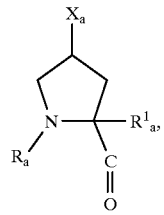

(VI$_a$)

wherein $R_a$ is hydrogen, or unsubstituted or fluorine-substituted alkyl; $R^1_a$ is hydrogen, alkyl, phenyl, or substituted phenyl; or $R_a$ and $R^1_a$ together form a propylene bridge; and $X_a$ is hydroxy, alkoxy or fluorine; or an α-amino acid of Formula VII$_a$,

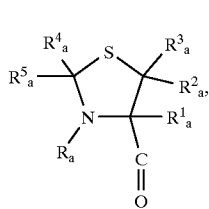

(VII$_a$)

wherein R$_a$ is hydrogen, or unsubstituted or fluorine-substituted alkyl; R$^1_a$ is hydrogen, alkyl, phenyl, or substituted phenyl; or R$_a$ and R$^1_a$ together form a propylene bridge; and R$^2_a$, R$^3_a$, R$^4_a$ and R$^5_a$ are each, independently, hydrogen or alkyl; or an α-amino acid residue of Formula VIII$_a$,

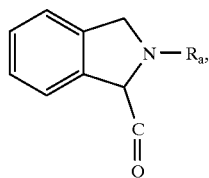

(VIII$_a$)

wherein R$_a$ is hydrogen, or unsubstituted or fluorine-substituted alkyl; or an α-amino acid residue of Formula IX$_a$,

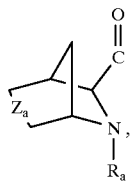

(IX$_a$)

wherein the 3-carbonyl moiety is in the endo or exo position, Z$_a$ is a single bond or a double bond, and R$_a$ is hydrogen or unsubstituted or fluorine-substituted alkyl; or an α-amino acid residue of Formula X$_a$,

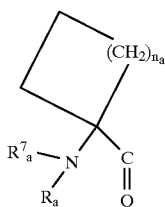

(X$_a$)

wherein n$_a$ is 1, 2 or 3, and R$^7_a$ is hydrogen or alkyl and R$_a$ is hydrogen, unsubstituted alkyl or fluorine-substituted alkyl;

B is a valyl, isoleucyl, allo-isoleucyl, norvalyl, 2-tert-butylglycyl or 2-ethylglycyl residue; or an α-amino acid residue of Formula II$_b$,

(II$_b$)

wherein R$^1_b$ is hydrogen, and R$^2_b$ is alkyl or alkenyl; or R$^1_b$ and R$^2_b$ together form an isopropylidene group;

D is an N-alkylvalyl, N-alkyl-2-ethylglycyl, N-alkyl-2-tert-butylglycyl, N-alkylnorleucyl, N-alkylisoleucyl, N-alkyl-allo-isoleucyl or N-alkylnorvalyl residue; or an α-amino acid residue of Formula II$_d$,

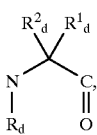

(II$_d$)

wherein R$_d$ is hydrogen, or unsubstituted or fluorine-substituted alkyl; R$^1_d$ is hydrogen; and R$^2_d$ is alkyl, substituted alkyl or alkenyl; or R$^1_d$ and R$^2_d$ together form an isopropylidene group; or an α-amino acid residue of Formula III$_d$,

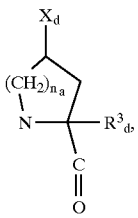

(III$_d$)

wherein nd is 1 or 2; R$^3_d$ is hydrogen, alkyl or fluorine-substituted alkyl; and X$_d$ is hydrogen; or n$_d$ is 1 and X$_d$ is fluorine, hydroxy, methoxy, or ethoxy;

E is a prolyl, thiazolidinyl-4-carbonyl, homoprolyl, or hydroxyprolyl residue; or an α-amino acid residue of Formula II$_e$,

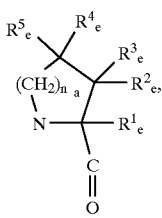

(II$_e$)

wherein n$_e$ is 0, 1 or 2, R$^1_e$ is hydrogen, or unsubstituted or fluorine-substituted alkyl; R$^2_e$ and R$^3_e$ are each, independently, hydrogen or alkyl; R$^4_e$ is hydrogen, hydroxy or alkoxy; and R$^5_e$ is hydrogen or fluorine; or n$_e$ is 1 and R$^3_e$ and R$^4_e$ together form a double bond; or n$_e$ is 1 and R$^4_e$ and R$^5_e$ together form a double-bonded oxygen diradical; or n$_e$ is 1 or 2 and R$^1_e$ and R$^2_e$ together form a double bond; or an aminocyclopentanecarboxylic acid residue of Formula III$_e$,

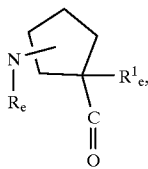
(III$_e$)

wherein R$_e$ is alkyl and R$^1_e$ is hydrogen, or unsubstituted or fluorine-substituted alkyl;

F is an azacycloalkanecarboxylic acid residue and

G is selected from the group consisting of hydrogen, alkyl, cycloalkyl, cycloalkylalkyl, aminocarbonylalkyl, aryl, arylalkyl, alkoxycarbonylalkyl, aryloxycarbonylalkyl, alkylsulfinylalkyl, alkylsulfonylalkyl, arylsulfinylalkyl, arylsulfonylalkyl, alkyl- or arylsulfinyl and alkyl- or arylsulfonyl; or F is an azacycloalkyl group and G is a heteroaryl group.

2. The compound of claim 1 wherein the pharmaceutically acceptable acid is selected from the group consisting of hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

3. The compound of claim 1 wherein F-G is an azacycloalkanecarboxylic acid of Formula II$_f$,

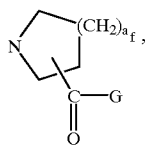
(II$_f$)

a$_f$ is 0, 1, or 2, and the carbonyl group is in the 1 or 2 position relative to the nitrogen atom.

4. The compound of claim 3 wherein G is a hydrogen atom, a normal or branched C$_1$–C$_8$-alkyl group, a halogen-substituted normal or branched C$_1$–C$_8$-alkyl group, a C$_3$–C$_8$-cycloalkyl group, or a C$_3$–C$_8$-cycloalkyl-C$_1$–C$_4$-alkyl group.

5. The compound of claim 3 wherein G is an arylalkyl or heteroarylalkyl group of Formula II$_g$, —(CH$_2$)a$_g$—R$^1_1$   (II$_g$), wherein a$_g$ is 0, 1 or 2, and R$^1_1$ is an aryl group, a substituted aryl group, wherein the aryl substituents comprise one or more halogen atoms, or one or more methoxy, ethoxy, trifluoromethyl, dioxymethylene, nitro, cyano, C$_1$–C$_7$-alkoxycarbonyl, C$_1$–C$_7$-alkylsulfonyl, amino, or C$_1$–C$_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline; where the heteroaryl substituents comprise one or more C$_1$–C$_6$-alkyl, hydroxyl or phenyl groups.

6. The compound of claim 3 wherein G is an alkoxycarbonylalkyl or aryloxycarbonylalkyl group of Formula III$_g$, —(CH$_2$)b$_g$—(C=O)c$_g$—OR$^2_1$   (III$_g$), b$_g$ is 1, 2, or 3, c$_g$ is 0 or 1, and R$^2_1$ is a hydrogen atom, a normal or branched C$_1$–C$_8$-alkyl group, a halogen-substituted normal or branched C$_1$–C$_8$-alkyl group, a C$_3$–C$_8$ cycloalkyl group, a C$_3$–C$_8$-cycloalkyl-C$_1$–C$_4$-alkyl group, an aryl group or a substituted aryl group, wherein the aryl substituents comprise one or more halogen atoms, or one or more methoxy, ethoxy, trifluoromethyl, dioxymethylene, nitro, cyano, C$_1$–C$_7$-alkoxycarbonyl, C$_1$–C$_7$-alkylsulfonyl, amino, or C$_1$–C$_7$-dialkylamino groups.

7. The compound of claim 3 wherein G is an aminocarbonylalkyl group of Formula IV$_g$,

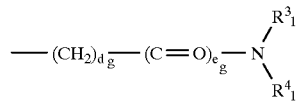
(IV$_g$)

d$_g$ is 1, 2, or 3, e$_g$ is 0 or 1, and R$^3_1$ and R$^4_1$ are each, independently, a hydrogen atom, a normal or branched C$_1$–C$_8$-alkyl group, a halogen-substituted normal or branched C$_1$–C$_8$-alkyl group, a C$_3$–C$_8$-cycloalkyl group, a C$_3$–C$_8$-cycloalkyl-C$_1$–C$_4$-alkyl group, an aryl group, a substituted aryl group, wherein the aryl substituents comprise one or more halogen atoms, or one or more methoxy, ethoxy, trifluoromethyl, dioxymethylene, nitro, cyano, C$_1$–C$_7$-alkoxycarbonyl, C$_1$–C$_7$-alkylsulfonyl, amino, or C$_1$–C$_7$-dialkylamino groups; or R$^3_1$, R$^4_1$ and the nitrogen atom form a ring system comprising 8 or fewer carbon atoms.

8. The compound of claim 3 wherein G is an alkylsulfinylalkyl or arylsulfinylalkyl group of Formula V$_g$, —(CH$_2$)g$_g$—S(O)h$_g$—R$^5_1$   (V$_g$), g$_g$ is 1 or 2, h$_g$ is 1 or 2, and R$^5_1$ is a methyl, trifluoromethyl, ethyl or phenyl group.

9. The compound of claim 3 wherein G is an alkyl- or arylcarbonylalkyl group of Formula VI$_g$, —(CH$_2$)i$_g$—(C=O)—R$^6_1$   (VI$_g$), wherein i$_g$ is 1 or 2; and R$^6_1$ is a hydrogen atom, a normal or branched C$_1$–C$_8$-alkyl group, which can be unsubstituted or substituted by up to six halogen atoms; a C$_3$–C$_8$-cycloalkyl group; a C$_3$–C$_8$-cycloalkyl-C$_1$–C$_4$-alkyl group; or a substituted or unsubstituted aryl or heteroaryl group.

10. The compound of claim 1 wherein F-G is an azacycloalkyl group of Formula III$_f$,

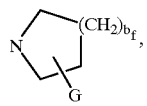
(III$_f$)

wherein b$_f$ is 0, 1, or 2 and G is a heteroaryl group in the 1 position relative to the nitrogen atom or in the 2 position relative to the nitrogen atom.

11. The compound of claim 10 wherein G is a heteroaryl group of Formula VII$_g$,

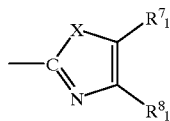
(VII$_g$)

wherein X is an NH group, an oxygen atom or a sulfur atom and $R^7_1$ and $R^8_1$ are each, independently, a hydrogen atom, a normal or branched $C_1$–$C_8$-alkyl group, a halogen-substituted normal or branched $C_1$–$C_8$-alkyl group, a $C_3$–$C_8$-cycloalkyl group or a $C_3$–$C_8$-cycloalkyl-$C_1$–$C_4$-alkyl group; or $R^7_1$ and $R^8_1$ are, independently, each a monovalent radical of Formula II$_l$,

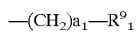
—(CH$_2$)a$_1$—R$^9_1$ (II$_l$), wherein a$_1$ is 0, 1, or 2, and $R^9_1$ is an aryl group, a substituted aryl group, wherein the aryl substituents comprise one or more halogen atoms, or one or more methoxy, ethoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline; wherein the heteroaryl substituents comprise one or more $C_1$–$C_6$-alkyl, hydroxyl or phenyl groups.

12. The compound of claim 10 wherein G is a heteroaryl group of Formula VIII$_g$,

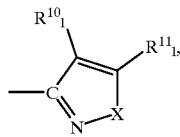
(VIII$_g$)

wherein X is an NR$^{12}_1$ group and $R^{12}_1$ is a hydrogen atom, a normal or branched $C_1$–$C_8$-alkyl group, which can be substituted by up to six halogen atoms, a $C_3$–$C_8$-cycloalkyl group, or a $C_3$–$C_8$-cycloalkyl-$C_1$–$C_4$-alkyl group; or X is an oxygen atom; $R^{10}_1$ and $R^{11}_1$ are each, independently, a hydrogen atom, a normal or branched $C_1$–$C_8$-alkyl group, a halogen-substituted normal or branched $C_1$–$C_8$-alkyl group, a $C_3$–$C_8$-cycloalkyl group or a $C_3$–$C_8$-cycloalkyl-$C_1$–$C_4$-alkyl group; or $R^{10}_1$ and $R^{11}_1$ are, independently, each a monovalent radical of Formula II$_l$,

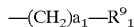
—(CH$_2$)a$_1$—R$^9_1$ (II$_l$), wherein a$_1$ is 0, 1, or 2, and $R^9_1$ is an aryl group, a substituted aryl group, wherein the aryl substituents comprise one or more halogen atoms, or one or more methoxy, ethoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline; wherein the heteroaryl substituents comprise one or more $C_1$–$C_6$-alkyl, hydroxyl or phenyl groups.

13. The compound of claim 10 wherein G is a aromatic diazo heterocyclic group of Formula IX$_g$,

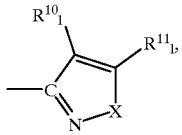
(VIII$_g$)

X is an NH group, an oxygen atom or a sulfur atom, and $R^{13}_1$ is a hydrogen atom, a normal or branched $C_1$–$C_8$-alkyl group, a halogen-substituted normal or branched $C_1$–$C_8$-alkyl group, a $C_3$–$C_8$-cycloalkyl group, or a $C_3$–$C_8$-cycloalkyl-$C_1$–$C_4$-alkyl group; or $R^{13}_1$ is a monovalent radical of Formula II$_l$,

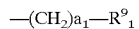
—(CH$_2$)a$_1$—R$^9_1$ (II$_l$), wherein a$_1$ is 0, 1, or 2, and $R^9_1$ is an aryl group, a substituted aryl group, wherein the aryl substituents comprise one or more halogen atoms, or one or more methoxy, ethoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline; wherein the heteroaryl substituents comprise one or more $C_1$–$C_6$-alkyl, hydroxyl or phenyl groups.

14. A pharmaceutical composition comprising a compound of claim 1.

15. A method for treating cancer in a mammal, comprising administering to the mammal a therapeutically effective amount of a compound of claim 1.

16. The method of claim 15 wherein the mammal is a human.

17. A compound of the formula

A-B-D-E-F-G, wherein A is N,N-dimethylvalyl, B is valyl, D is N-methylvalyl, E is prolyl, and F-G is of Formula III$_f$,

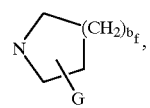
(III$_f$)

wherein b$_f$ is 1 or 2 and G is a heteroaryl group of Formula VII$_g$,

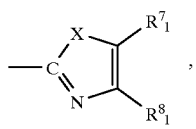
(VII$_g$)

wherein X is NH, oxygen or sulfur, and $R^8_1$ are each, independently, a hydrogen atom, a normal or branched $C_1$–$C_8$-alkyl group, a halogen-substituted normal or branched $C_1$–$C_8$-alkyl group, a $C_3$–$C_8$-cycloalkyl group or a $C_3$–$C_8$-cycloalkyl-$C_1$–$C_4$-alkyl group; or $R^7_1$ and $R^8_1$ are, independently, each a monovalent radical of Formula $II_l$,

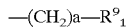                                                     ($II_l$), wherein $a_1$ is 0, 1, or 2, and $R^9_1$ is an aryl group, a substituted aryl group, wherein the aryl substituents comprise one or more halogen atoms, or one or more methoxy, ethoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline; wherein the heteroaryl substituents comprise one or more $C_1$–$C_6$-alkyl, hydroxyl or phenyl groups.

18. A compound of the formula

A-B-D-E-F-G, wherein A is N,N-dimethylvalyl, B is valyl, D is N-methylvalyl, E is prolyl, and F-G is of Formula $III_f$,

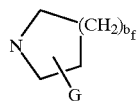                                    ($III_f$)

wherein $b_f$ is 1 or 2 and G is a heteroaryl group of Formula $VIII_g$,

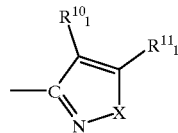                                    ($VIII_g$)

wherein X is an $NR^{12}_1$ group and $R^{12}_1$ is a hydrogen atom, a normal or branched $C_1$–$C_8$-alkyl group, which can be substituted by up to six halogen, a $C_3$–$C_8$-cycloalkyl group, or a $C_3$–$C_8$-cycloalkyl-$C_1$–$C_4$-alkyl group; or X is an oxygen atom; $R^{10}_1$ and $R^{11}_1$ are each, independently, a hydrogen atom, a normal or branched $C_1$–$C_8$-alkyl group, a halogen-substituted normal or branched $C_1$–$C_8$-alkyl group, a $C_3$–$C_8$-cycloalkyl group or a $C_3$–$C_8$-cycloalkyl-$C_1$–$C_4$-alkyl group; or $R^{10}_1$ and $R^{11}_1$ are, independently, each a monovalent radical of Formula $II_l$,

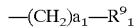                                                     ($II_l$), wherein $a_1$ is 0, 1, or 2, and $R^9_1$ is an aryl group, a substituted aryl group, wherein the aryl substituents comprise one or more halogen atoms, or one or more methoxy, ethoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline; wherein the heteroaryl substituents comprise one or more $C_1$–$C_6$-alkyl, hydroxyl or phenyl groups.

19. A compound of the formula

A-B-D-E-F-G, wherein A is N,N-dimethylvalyl, B is valyl, D is N-methylvalyl, E is prolyl, and F-G is of Formula $III_f$,

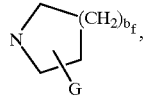                                    ($III_f$)

wherein $b_f$ is 1 or 2 and G is an aromatic diazo group of Formula $IX_g$,

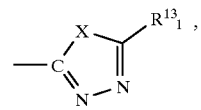                                    ($IX_g$)

wherein X is NH, oxygen or sulfur, and $R^{13}_1$ is a hydrogen atom, a normal or branched $C_1$–$C_8$-alkyl group, a halogen-substituted normal or branched $C_1$–$C_8$-alkyl group, a $C_3$–$C_8$-cycloalkyl group, or a $C_3$–$C_8$-cycloalkyl-$C_1$–$C_4$-alkyl group; or $R^{13}_1$ is a monovalent radical of Formula $II_l$,

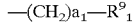                                                     ($II_l$), wherein $a_1$ is 0, 1, or 2, and $R^9_1$ is an aryl group, a substituted aryl group, wherein the aryl substituents comprise one or more halogen atoms, or one or more methoxy, ethoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl or substituted heteroaryl group derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline; wherein the heteroaryl substituents comprise one or more $C_1$–$C_6$-alkyl, hydroxyl or phenyl groups.

20. A compound of the formula

A-B-D-E-F-G wherein A is N,N-dimethylvalyl, B is valyl, D is N-methylvalyl, E is prolyl, and F-G is of Formula $II_f$,

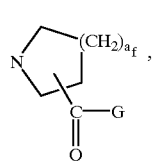                                    ($II_f$)

wherein $a_f$ is 1 or 2 and G is a monovalent radical selected from the group consisting of hydrogen, alkyl, cycloalkyl, cycloalkylalkyl, aminocarbonylalkyl, arylalkyl, heteroarylalkyl, alkoxycarbonylalkyl, aryloxycarbonylalkyl, alkylsulfinylalkyl, alkylsulfonylalkyl, arylsulfinylalkyl, arylsulfonylalkyl, alkyl- or arylsulfinyl, alkyl- or arylsulfonyl, substituted or unsubstituted aryl and substituted or unsubstituted heteroaryl.

21. The compound of claim 20 wherein $a_f$ is 1 and G is phenyl.

* * * * *

UNITED STATES PATENT AND TRADEMARK OFFICE
CERTIFICATE OF CORRECTION

PATENT NO. : 5,965,537
DATED : October 12, 1999
INVENTOR(S) : Kurt Ritter, Wilhelm Amberg, Teresa Barlozzari, Andreas Haupt, Bernd Janssen and Andreas Kling It is certified that error appears in the above-indentified patent and that said Letters Patent is hereby corrected as shown below:

Column 39, line 28: delete "Formula II$_l$" and substitute therefor --Formula II$_a$--.

Column 42, line 36: delete " 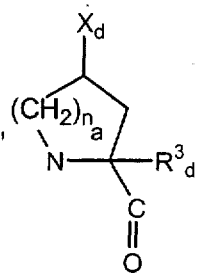 " and substitute therefor -- 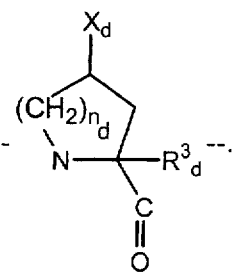 --.

Column 42, line 43: delete "nd" and substitute therefor --n$_d$--.

Column 42, line 54: delete " 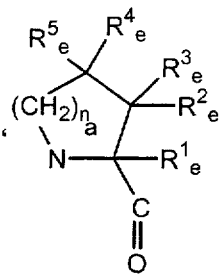 " and substitute therefor --

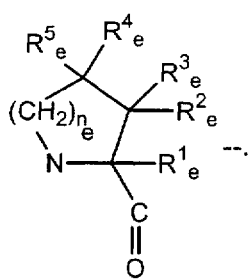 --.

UNITED STATES PATENT AND TRADEMARK OFFICE
CERTIFICATE OF CORRECTION

PATENT NO. : 5,965,537
DATED : October 12, 1999
INVENTOR(S) : Kurt Ritter, Wilhelm Amberg, Teresa Barlozzari, Andreas Haupt, Bernd Janssen and Andreas Kling It is certified that error appears in the above-identified patent and that said Letters Patent is hereby corrected as shown below:

Column 44, line 48: delete "$i_{g\ is}$" and substitute therefor --$i_g$ is--.

Column 46, line 5: delete " 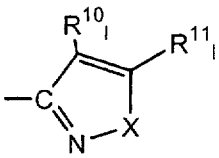 $(VIII_g)$ " and substitute therefor

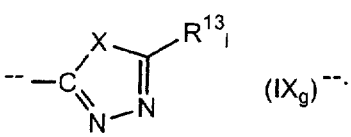 $(IX_g)$ --.

Column 46, line 66: after "sulfur," insert --and $R^7_1$--.

UNITED STATES PATENT AND TRADEMARK OFFICE
CERTIFICATE OF CORRECTION

PATENT NO. : 5,965,537
DATED : October 12, 1999
INVENTOR(S) : Kurt Ritter, Wilhelm Amberg, Teresa Barlozzari, Andreas Haupt, Bernd Janssen and Andreas Kling It is certified that error appears in the above-identified patent and that said Letters Patent is hereby corrected as shown below:

Column 47, line 6: delete "-$(CH_2)a$-$R^9_1$" and substitute therefor --$(CH_2)a_1$-$R^9_1$--.

Signed and Sealed this

Tenth Day of October, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 5 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:1:

Val Val Val Pro Xaa
   1               5

(2) INFORMATION FOR SEQ ID NO:2:

(i) SEQUENCE CHARACTERISTICS:
       (A) LENGTH: 4 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:2:

Val Val Val Pro
   1

(2) INFORMATION FOR SEQ ID NO:3:

```
(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:3:

Val Val Val Pro Pro
1               5
```